United States Patent
Braren et al.

(10) Patent No.: US 7,897,153 B1
(45) Date of Patent: Mar. 1, 2011

(54) CHIMERA OF HUMAN IGE RECEPTOR α-CHAIN AND AVIAN CONSTANT IMMUNO-GLOBULIN DOMAINS FOR THE DETERMINATION OF SERUM IGE

(75) Inventors: Ingke Braren, Hamburg (DE); Reinhard Bredehorst, Hamburg (DE); Thomas Grunwald, Hamburg (DE)

(73) Assignee: PLS-Design GmbH, Hamburg (DE)

( * ) Notice: Subject to any disclaimer, the term of this patent is extended or adjusted under 35 U.S.C. 154(b) by 533 days.

(21) Appl. No.: 11/581,874

(22) Filed: Oct. 17, 2006

(30) Foreign Application Priority Data

Oct. 17, 2005 (EP) .................................. 05022582

(51) Int. Cl.
*A61K 39/00* (2006.01)
(52) U.S. Cl. ............... 424/192.1; 424/133.1; 424/157.1; 424/185.1; 530/387.1; 530/687.3; 536/23.1; 435/328
(58) Field of Classification Search ........................ None
See application file for complete search history.

(56) References Cited

U.S. PATENT DOCUMENTS

| 5,945,294 A * | 8/1999 | Frank et al. ..................... 435/7.9 |
| 6,608,172 B1 * | 8/2003 | Chiou ........................... 530/413 |
| 6,737,056 B1 * | 5/2004 | Presta ........................ 424/133.1 |
| 2005/0221424 A1 | 10/2005 | Utku | |

FOREIGN PATENT DOCUMENTS

WO    WO 98/23964    6/1998

OTHER PUBLICATIONS

Chamow et al., Tibtech, 1996, 14:52-60.*
Shimamoto et al., Biologicals, Sep. 2005, 33:169-174.*
Basu M, Hakimi J, Dharm E, Kondas AJ, Tsien WH, Pilson RS, Lin P, Gilfillan A, Haring P, Braswell EH, et al. Purification and characterization of human recombinant IgE-Fc fragments that bind to the human high affinity IgE receptor. J. Biol. Chem. 268, 13118-13127, 1993.
Beasley R, Crane J, Lai CK, Pearce N. Prevalence and etiology of asthma. J. Allergy Clin. Immunol. 105: 466-472, 2000.
Blank U, Ra C, Kinet J-P. Characterization of truncated α chain products from human, rat, and mouse high affinity receptor for immunoglobulin E. J. Biol. Chem. 266, 2639-2646, 1991.
Boscato L, Stuart M. Incidence and Specificity of interference in Two-site immunoassays. Clin. Chem.. 32, 1491-1495, 1986.
Boscato LM, Stuart MC. Heterophilic antibodies: a problem for all immunoassays. Clin. Chem. 34, 27-33, 1988.
Burrows B, Martinez FD, Halonen M, Barbee RA, Cline MG. Association of asthma with serum IgE levels and skin-test reactivity to allergens. N. Engl. J. Med. 320: 271-277, 1989.
Campbell RD, Dodds AW, Porter RR. The binding of human complement component C4 to antibody-antigen aggregates. Biochem. J. 189, 6780, 1980.
Conrad DH. Fc epsilon RII/CD23: the low affinity receptor for IgE. Ann. Rev. Immunol. 8: 623-645, 1990.
Doyle R. Asthma worldwide. Sci. Am. 282: 30, 2000.
Figdor CG, van Kooyk Y, Adema GJ. C-Type lectin receptors on dendritic cells and Langerhans cells. Nature Rev. Immunol. 2, 77-84, 2002.
Garman SC, Kinet J-P, Jardetzky TS. The crystal structure of the human high-affinity IgE receptor (FcεRIα). Annu. Rev. Immunol. 17: 973-976, 1999.
Haak-Frendscho M, Ridgway J, Shields R, Robbins K, Gorman C, Jardieu P. Human IgE receptor α-chain IgG chimera blocks passive cutaneous anaphylaxis reaction in vivo. J. Immunol. 151: 351-358, 1993.
Hamelmann E, Rolinck-Werninghaus C, Wahn U. From IgE to anti-IgE: where do we stand? Allergy 57: 983-994, 2002.
Hamelmann E, Rolinck-Weminghaus C, Wahn U. Is there a role for anti-IgE in combination with specific allergen immunotherapy? Curr. Opin. Allergy Clin. Immunol. 3: 501-510, 2003.
Hara T, Yamada K, Tachibana H. Basophilic differentiation of the human leukemia cell line KU812 upon treatment with interleukin-4. Biochem. Biophys. Res. Commun. 247: 542, 1998.
Hodek and Stiborova Chicken Antibodies—Superior Alternative for Conventional Immunoglobulins. Proc. Indian Nat. Sci. Acad. B69 No. 4 pp. 461-468, 2003.
Johnson PM, Faulk WP: Rheumatoid factor: its nature, specificity, and production in rheumatoid arthritis. Clin. Immunol. Immunopathol. 6, 414-430, 1976.
Kapyaho K, Tanner P, Weber T. Effect of complement binding on a solid-phase immunometric TSH assay. Scand. J. Clin. Lab. Invest. 49, 211215, 1989.
Kinet J-P. The high-affinity IgE receptor (FcεRI): from physiology to pathology, Annu. Rev. Immunol. 17: 931-972, 1999.
Kricka U. Human anti-animal antibody interferences in immunological assays. Clin. Chem. 45, 942-956, 1999.
Larsson A, Sjoquist J. Binding of complement components Clq, C3, C4 and C5 to a model immune complex in ELISA. J. Immunol. Methods 119, 103-109, 1989.
Larsson A, Karlsson-Parra A, Sjoquist J. Use of chicken antibodies in enzyme immunoassays to avoid interference by rheumatoid factors. Clin. Chem. 37, 411-414, 1991.
Larsson A, Mellstedt H. Chicken antibodies: a tool to avoid interference by human anti-mouse antibodies in ELISA after in vivo treatment with murine monoclonal antibodies. Hybridoma 11, 33-39, 1992.
Larsson A, Wejaker PE, Forsberg PO, Lindahl T. Chicken antibodies: a tool to avoid interference by complement activation in ELISA. J. Immunol. Methods 156, 79-83, 1992.
Leslie GA, Clem LW. Phylogen of immunoglobulin structure and function. Immunoglobulins of the chicken. J. Exp. Med. 130, 1337-1352, 1969. Letourner O, Sechi S, Wilette-Brown J, Robertson MW, Kinet JP. Glycosylation of human truncated FcεRIα-chain is necessary for efficient folding in the endoplasmic reticulum. J. Biol. Chem. 270: 8249-8256, 1995.
Lowe J, Jardieu P, VanGorp K, Fei DT. Allergen-induced histamine release in rat mast cells transfected with the alpha subunits of Fc epsilon RI. J. Immunol. Meth. 184: 113, 1995.
Malhotra R., Wormald MR, Rudd PM, Fischer PB, Dwek RA, Sim RB. Glycosylation changes of IgG associated with rheumatoid arthritis can activate complement via the mannose-binding protein. Nat. Med. 1, 237-243, 1995.

(Continued)

*Primary Examiner* — Michael Szperka

(74) *Attorney, Agent, or Firm* — Ballard Spahr LLP

(57) ABSTRACT

The instant application inter alia relates to chimeric fusion constructs comprising the extracellular portion of human FcεRIα and at least one avian constant immunoglobulin domain and the use thereof for in vitro diagnostic purposes.

19 Claims, 17 Drawing Sheets

OTHER PUBLICATIONS

Figure 2:
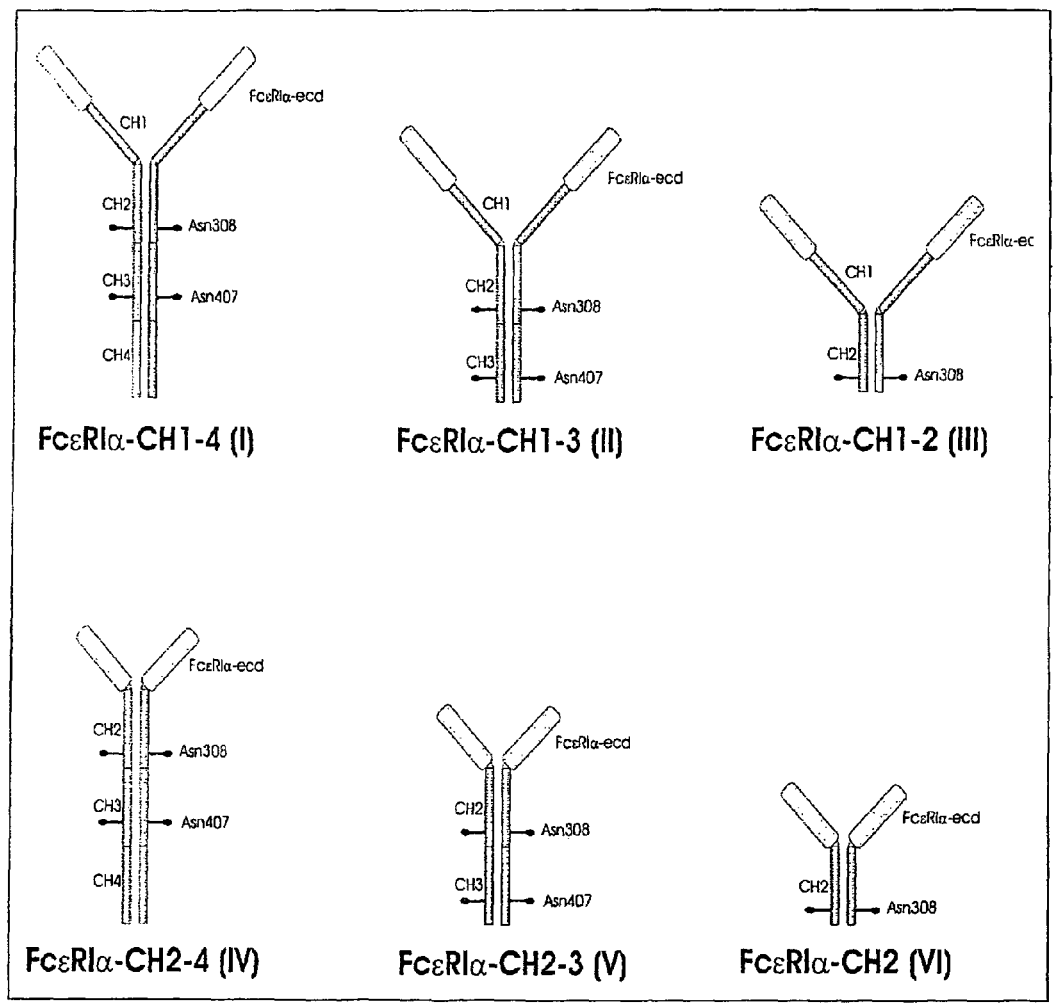

Ostergaard PA, Ebbesen F, Nolte H, Skov PS. Basophil histamine release in the diagnosis of house dust mite and dander allergy of asthmatic children. Comparison between prick test, RAST, basophil histamine release and bronchial provocation. Allergy 45: 231, 1990.

Presta LG, Lahr SJ, Shields RL, et al. Humanization of an antibody directed against IgE. J Immunol 151: 2623-2632, 1993.

Pruzansky JJ, Grammer LC, Patterson R, Roberts M. Dissociation of IgE from receptors on human basophils. Enhanced passive sensitization for histamine release. J. Immunol. 131: 1949, 1983.

Ravetch JV, Kinet J-P. Fc receptors. Annu. Rev. Immunol. 9: 457, 1991.

Reid, M.J., Moss, R.B., Hsu, Y.P., Kwasnicki, J.M., Commerford, T.M., Nelson, B.L. Seasonal asthma in northern California: allergic causes and efficacy of immunotherapy. J. Allergy Clin. Immunol. 78, 590-600, 1986.

Robertson MW. Phage and *Escherichia coli* expression of the human high affinity immunoglobulin E receptor alpha-subunit ectodomain. Domain localization of the IgE-binding site. J. Biol. Chem. 268: 12736-12743, 1993.

Roos A, Bouwman LH, van Gijlswijk-Janssen DJ, Faber-Krol MC, Fallaux-van den Houten FC, Klar-Mohamad N, Hack CE, Tilanus MG, Daha MR. Human IgA activates the complement system via the mannan-binding lectin pathway. J. Immunol. 167, 2861-.

Saban R, Haak-Frendscho M, Zine M, et al. Human FcεRI-IgG and humanized anti-IgE monoclonal antibody MaE11 block passive sensitization of human and rhesus monkey lung. J. Allergy Clin. Immunol. 94: 836-843, 1994.

Scarselli E, Esposito G, Traboni C. Receptor phage. Display of functional domains of the human high affinity IgE receptor on the M13 phage surface. FEBS Lett. 329: 223-226, 1993.

Schade et al. Chicken Egg Yolk antibodies (IgY-technology): A Review of Progress in Production and Use in Research and Human and Veterinary Medicine. ATLB 33, 129-154, 2005.

Sun S, Mo W, Il Y, Liu S. Preparation and mass spectrometric study of egg yolk antibody (IgY) against rabies virus. Rapid Commun. Mass. Spectrom. 15, 708-712, 2001.

Suzuki N, Khoo KH, Chen CM, Chen CH, Lee YC. N-glycan structures of pigeon IgG: a major serum glycoprotein containing Galα1-4Gal termini J. Biol. Chem. 278, 46293-46306, 2003.

Suzuki N, Lee YC. Site-specific N-glycosylation of chicken serum IgG. Glycobiology 14, 275-292, 2004.

Takahashi N, Nakagawa H, Fujikawa K, Kawamura Y, Tomiya N. Three-dimensional elution mapping of pyridylaminated N-linked neutral and sialyl oligosaccharides. Anal. Biochem. 226, 139-146, 1995.

Van de Wetering JK., van Golde LMG, Batenburg JJ. Collectins: Players of the innate immune system. Eur. J. Biochem. 271, 1229-1249, 2004.

Varney, V.A., Hamid, Q.A., Gaga, M., et al. Influence of grass pollen immunotherapy on cellular infiltration and cytokine mRNA expression during allergen-induced late-phase cutaneous responses. J. Clin. Invest. 92, 644-651, 1993.

Verma R, Boleti E, George AJT. Antibody engineering: Comparison of bacterial, yeast, insect and mammalian expression systems. J. Immunol. Meth. 216: 165-181, 1998.

Wan T, Beavil RL, Fabiane SM, Beavil AJ, Sohi MK, Keown M, Young RJ, Henry AJ, Owens RJ, Gould HJ, Sutton BJ. The crystal structure of IgE Fc reveals an asymmetrically bent conformation. Nat. Immunol. 3, 681-686, 2002.

Warr GW, Magor KE, Higgins DA. IgY: clues to the origins of modern antibodies. Immunol. Today 16, 392-398, 1995.

Andris-Widhopf J, Rader C, Steinberger P, Fuller R, Barbas CF 3rd. (2000) Methods for the generation of chicken monoclonal antibody fragments by phage display. J. Immunol. Methods, 242(1-2): 159-81.

Arbabi Ghahroudi M, Desmyter A, Wyns L, Hamers S, Muyldermans S. (1997) Selection and identification of single domain antibody fragments from camel heavy-chain antibodies. FEBS Letts., 414: 521-26.

Davies EL, Smith JS, Birkett CR, Manser JM, Anderson-Dear DV, Young JR. (1995) Selection of specific phage-display antibodies using libraries derived from chicken immunoglobulin genes. J. Immunol Methods, 186(1): 125-35.

Greunke et al. (2006) J. Biotechnology 124: 446-456.

Larsson A, Lindahl TL. Chicken antibodies: a tool to avoid interference, in immunological assays, Avian Immunology in Progress. Tours (France), Ed. Inra, Aug. 31-Sep. 2, 1993 (Les Colloques, No. 62, pp. 97-102).

Nishinaka S, Matsuda H, Murata M. (1989) Establishment of a chicken X chicken hybridoma secreting specific antibody. Int. Arch. Allergy Appl. Immunol., 89(4): 416-9.

Nishinaka S, Akiba H, Nakamura M, Suzuki K, Suzuki T, Tsubokura K, Horiuchi H, Furusawa S, Matsuda H. (1996) Two chicken B cell lines resistant to ouabain for the production of chicken monoclonal antibodies. J. Vet. Med. Sci., 58(11): 1053-56.

Olovsson M, Larsson A. (1993), Biotin Labelling of Chicken Antibodies and their subsequent use in ELISA and immunohistochemistry. Comp. Immun. Microbiol. Infect. Dis., 16(2): 145-152.

Randolf et al. (1999) Recombinant Antibodies: Applications in Plant Science and Plant Pathology, Taylor and Francis Inc., Philadelphia PA, Chapter 4, pp. 57-60.

Ryabova et al. (1997) Nat. Biotech. 15: 79-84.

Restriction Requirement mailed on Jan. 31, 2007 (U.S. Appl. No. 11/510,329).

Response to Restriction Requirement filed on Jul. 3, 2007 (U.S. Appl. No. 11/510,329).

Non-Final Office Action mailed on Aug. 9, 2007 (U.S. Appl. No. 11/510,329).

Amendment Response to Non-Final Office Action filed on Feb. 11, 2008 (U.S. Appl. No. 11/510,329).

Final Office Action mailed on May 13, 2008 (U.S. Appl. No. 11/510,329).

Examiner's Interview Summary of Interview conducted on Aug. 27, 2008 (U.S. Appl. No. 11/510,329).

Request for Continued Examination filed on Sep. 12, 2008(U.S. Appl. No. 11/510,329).

Amendment and Response to Office Action submitted with Request for Continued Examination filed on Sep. 12, 2008 (U.S. Appl. No. 11/510,329).

Non-Final Office Action mailed on Nov. 28, 2008 (U.S. Appl. No. 11/510,329).

Amendment and Response to Non-Final Office Action filed on Mar. 2, 2009 (U.S. Appl. No. 11/510,329).

Final Office Action mailed on Jun. 24, 2009(U.S. Appl. No. 11/510,329).

Amendment and Response after Final Office Action filed on Sep. 24, 2009 (U.S. Appl. No. 11/510,329).

Notice of Allowance mailed on Nov. 2, 2009 (U.S. Appl. No. 11/510,329).

Examiner Interview Summary for interview conducted on Dec. 9, 2009 (U.S. Appl. No. 11/510,329).

Issue Notification mailed on Mar. 24, 2010 (U.S. Appl. No. 11/510,329).

* cited by examiner

Figure 1

A:

Fc epsilon receptor alpha subunit coding region

```
atggctcctgccatg
 M   A   P   A   M
gaatcccctactctactgtgtgtagccttactgttcttcgctccagatggcgtgttagca
 E   S   P   T   L   L   C   V   A   L   L   F   F   A   P   D   G   V   L   A
gtccctcagaaacctaaggtctccttgaaccctccatggaatagaatatttaaagagag
 V   P   Q   K   P   K   V   S   L   N   P   P   W   N   R   I   E   K   C   E
aatgtgactcttacatgtaatgggaacaatttctttgaagtcagttccaccaaatggttc
 N   V   T   L   T   C   N   G   N   N   F   F   E   V   S   S   T   K   W   F
cacaatggcagcctttcagaagagacaaattcaagtttgaatatgtgaatgccaattt
 H   N   G   S   L   S   E   E   T   N   S   S   L   N   I   V   N   A   K   F
gaagacagtggagaatacaaatgtcagcaccaacaagttaatgagagtgaacctgtgtac
 E   D   S   G   E   Y   K   C   Q   H   Q   Q   V   N   E   S   E   P   V   Y
ctggaagtcttcagtgactggctgctccttcaggcctctgctgaggtggtgatggagggc
 L   E   V   F   S   D   W   L   L   L   Q   A   S   A   E   V   V   M   E   G
cagccctcttcctcaggtgccatggttggaggactggatgtgtacaagtgatctat
 Q   P   L   F   L   R   C   H   G   W   R   N   W   D   V   Y   K   V   I   Y
tataaggatggtgaagctctcaagtactggtatgagaaccacaacatctccattacaaat
 Y   K   D   G   E   A   L   K   Y   W   Y   E   N   H   N   I   S   I   T   N
gccacagttgaagacagtggaacctactactgtacgggcaaagtgtggcagctggactat
 A   T   V   E   D   S   G   T   Y   Y   C   T   G   K   V   W   Q   L   D   Y
gagtctgagcccctcaacattactgtaataaaagctccgcgtgagaagtactggctacaa
 E   S   E   P   L   N   I   T   V   I   K   A   P   R   E   K   Y   W   L   Q
ttttttatcccattgttggtggtgattctgtttgctgtggacacaggattatttatctca
 F   F   I   P   L   L   V   V   I   L   F   A   V   D   T   G   L   F   I   S
actcagcagcaggtcacatttctcttgaagattaagagaaccaggaaaggcttcagactt
 T   Q   Q   Q   V   T   F   L   L   K   I   K   R   T   R   K   G   F   R   L
ctgaacccacatcctaagccaaaccccaaaaacaactga
 L   N   P   H   P   K   P   N   P   K   N   N   -
```

Figure 1

B:

upsilon heavy chain constant region coding region

```
cgcgagc
cccacatcgc cccccgatt gtaccctcta tccgcctgtt gttccgactc ggctgtcccg
ccggccgtgg gctgcctgtt gtccccttcg tccgccggcg gcatctcctg ggagggctcc
ggaggtacgg cggtggccgg cagagtttcg gggaccccg tgaagctcag cttcgtccgc
ctcagccccg gcgagaagag gaaaagcttc gtctgcagcg ccgccccgg gggggcgctg
ctcaaaaagg aggtgcaggt ctgccgggta gatcccgtac cgcctgtagc cccagaggtg
caggtcctcc acccctcctc ctgcaccccg agccaatccg agtcggtgga gctgttgtgt
ttggtgacgg ggttctcccc ggcgtcggcg gaggtcgaat ggttggtgga cggagtgggg
ggacttttgg tggcctccca aagcccggcg gtccgcagcg gatccaccta cagcctgagc
agccgcgtca acgtcagcgg caccgattgg agggaaggga agagttacag ctgtagggtg
aggcaccccg caaccaacac cgtggtggag gatcacgtca agggatgccc ggacggcgct
cagagctgca gccccatcca gctgtacgcc atcccaccca gcccgggcga gctgtacatc
agcttagacg ccaaactgag gtgcctggtg gtcaacctgc ccagcgattc cagcctcagc
gtcacctgga ccagggagaa gagtgggaac ctccggcccg acccgatggt cctccaagaa
cacttcaacg gcacctacag cgccagcagc gccgtcccc tcagcaccca ggattggtta
tccggggaga ggttcacctg caccgtgcag cacgaggagc tgcccctgcc gctcagcaag
agcgtctaca ggaacacggg acccaccacc ccacctctga tctaccct cgccccccac
ccggaagagc tgtccctctc ccgcgtcacc ctgagctgcc tggtccgcgg cttccgccca
cgtgacatcg agatccggtg gctccgcgac caccgcgccg ttcccgccac cgaattcgtc
accaccgccg tcctcccgga agagagaacc gcaaacggcg ccggcggtga cggcgacacc
ttcttcgtgt acagtaagat gagcgtggag accgccaagt ggaacggcgg gacggtgttc
gcctgcatgg cggtgcacga ggcgctgccc atgcgcttca gccagcgcac gctgcagaaa
caggctggta aataa
```

Figure 1

C:

Chimera providing CH1-CH4 region

```
gtccctcagaaacctaaggtctccttgaaccctccatggaatagaatatttaaaggagag
 V  P  Q  K  P  K  V  S  L  N  P  P  W  N  R  I  F  K  G  E
aatgtgactcttacatgtaatgggaacaatttctttgaagtcagttccaccaaatggttc
 N  V  T  L  T  C  N  G  N  N  F  F  E  V  S  S  T  K  W  F
cacaatggcagcctttcagaagagacaaattcaagtttgaatattgtgaatgccaaattt
 H  N  G  S  L  S  E  E  T  N  S  S  L  N  I  V  N  A  K  F
gaagacagtggagaatacaaatgtcagcaccaacaagttaatgagagtgaacctgtgtac
 E  D  S  G  E  Y  K  C  Q  H  Q  Q  V  N  E  S  E  P  V  Y
ctggaagtcttcagtgactggctgctccttcaggcctctgctgaggtggtgatggagggc
 L  E  V  F  S  D  W  L  L  L  Q  A  S  A  E  V  V  M  E  G
cagcccctcttcctcaggtgccatggttggaggaactgggatgtgtacaaggtgatctat
 Q  P  L  F  L  R  C  H  G  W  R  N  W  D  V  Y  K  V  I  Y
tataaggatggtgaagctctcaagtactggtatgagaaccacaacatctccattacaaat
 Y  K  D  G  E  A  L  K  Y  W  Y  E  N  H  N  I  S  I  T  N
gccacagttgaagacagtggaacctactactgtacgggcaaagtgtggcagctggactat
 A  T  V  E  D  S  G  T  Y  Y  C  T  G  K  V  W  Q  L  D  Y
gagtctgagcccctcaacattactgtaataaaagctccgggcgcgcccgcgagccccaca
 E  S  E  P  L  N  I  T  V  I  K  A  P  G  A  P  A  S  P  T
tcgccccccgattgtaccctctatccgcctgttgttccgactcggctgtcccgccggcc
 S  P  P  R  L  Y  P  L  A  C  C  S  D  S  A  V  P  P  A
gtgggctgcctgttgtccccttcgtccgccggcggcatctcctggggagggctccggaggt
 V  G  C  L  L  S  P  S  S  A  G  G  I  S  W  E  G  S  G  G
acggcggtggccggcagagtttcggggaccccgtgaagctcagcttcgtccgcctcagc
 T  A  V  A  G  R  V  S  G  T  P  V  K  L  S  F  V  R  L  S
cccggcgagaagaggaaaagcttcgtctgcagcgccgcccccggggggcgctgctcaaa
 P  G  E  K  R  K  S  F  V  C  S  A  A  P  G  G  A  L  L  K
aaggaggtgcaggtctgccggggtagatcccgtaccgcctgtagccccagaggtgcaggtc
 K  E  V  Q  V  C  R  V  D  P  V  P  P  V  A  P  E  V  Q  V
ctccaccccctcctcctgcaccccgagccaatccgagtcggtggagctgttgtgtttggtg
 L  H  P  S  S  C  T  P  S  Q  S  E  V  E  L  L  C  L  V
acggggttctccccggcgtcggcggaggtcgaatggttggtggacggagtggggggactt
 T  G  F  S  P  A  S  A  E  V  E  W  L  V  D  G  V  G  G  L
ttggtggcctcccaaagccggcggtccgcagcggatccacctacagcctgagcagccgc
 L  V  A  S  Q  P  A  V  R  S  G  S  T  Y  S  L  S  S  R
gtcaacgtcagcggcaccgattggagggaagggaagagttacagctgtagggtgaggcac
 V  N  V  S  G  T  D  W  R  E  G  K  S  Y  S  C  R  V  H
cccgcaaccaacaccgtggtggaggatcacgtcaagggatgcccggacggcgctcagagc
 P  A  T  N  T  V  V  E  D  H  V  K  G  C  P  D  G  A  Q  S
tgcagccccatccagctgtacgccatcccaccagcccggcgagctgtacatcagctta
 C  S  P  I  Q  L  Y  A  I  P  P  S  P  G  E  L  Y  I  S  L
gacgccaaactgaggtgcctggtggtcaacctgcccagcgattccagcctcagcgtcacc
 D  A  K  L  R  C  L  V  V  N  L  P  S  D  S  S  L  S  V  T
tggaccagggagaagagtgggaacctccggcccgacccgatggtcctccaagaacacttc
 W  T  R  E  K  S  G  N  L  R  P  D  P  M  V  L  Q  E  H  F
aacggcacctacagcgccagcagcgccgtcccgtcagcacccaggattggttatccggg
 N  G  T  Y  S  A  S  S  A  V  P  V  S  T  Q  D  W  L  S  G
gagaggttcacctgcaccgtgcagcacgaggagctgccctgccgctcagcaagagcgtc
 E  R  F  T  C  T  V  Q  H  E  E  L  P  L  P  L  S  K  S  V
tacaggaacacgggacccaccaccccacctctgatctacccttcgcccccacccggaa
 Y  R  N  T  G  P  T  T  P  P  L  I  Y  P  F  A  P  H  P  E
gagctgtccctctcccgcgtcaccctgagctgcctggtccgcggcttccgcccacgtgac
 E  L  S  L  S  R  V  T  L  S  C  L  V  R  G  F  R  P  R  D
atcgagatccggtggctccgcgaccaccgcgccgttcccgccaccgaattcgtcaccacc
 I  E  I  R  W  L  R  D  H  R  A  V  P  A  T  E  F  V  T  T
```

Figure 1 C - Continued

```
gccgtcctcccggaagagagaaccgcaaacggcgccggcggtgacggcgacaccttcttc
  A  V  L  P  E  E  R  T  A  N  G  A  G  G  D  G  D  T  F  F
gtgtacagtaagatgagcgtggagaccgccaagtggaacggcgggacggtgttcgcctgc
  V  Y  S  K  M  S  V  E  T  A  K  W  N  G  G  T  V  F  A  C
atggcggtgcacgaggcgctgcccatgcgcttcagccagcgcacgctgcagaaacaggct
  M  A  V  H  E  A  L  P  M  R  F  S  Q  R  T  L  Q  K  Q  A
ggtaaacatcaccatcactga
  G  K  H  H  H  H  -
```

Fig. 10
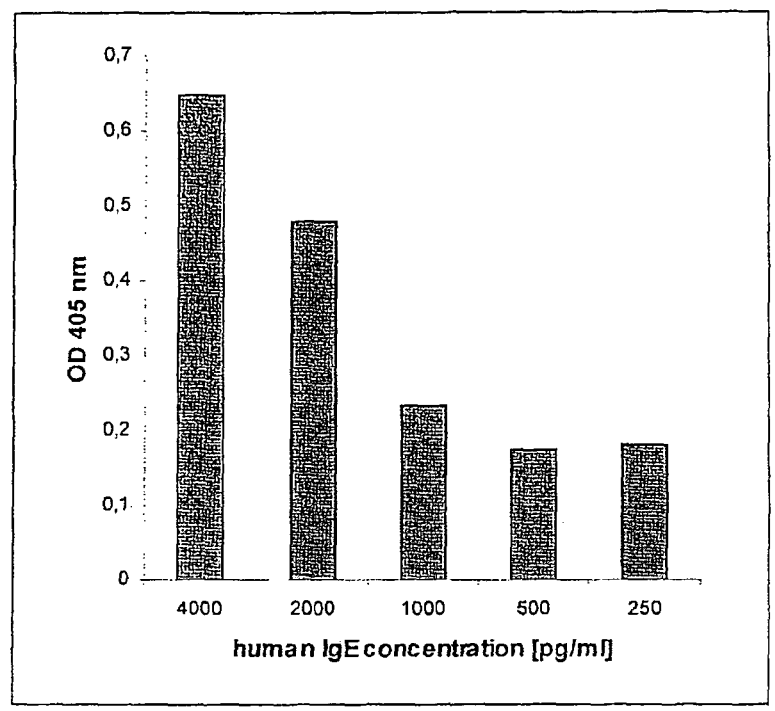
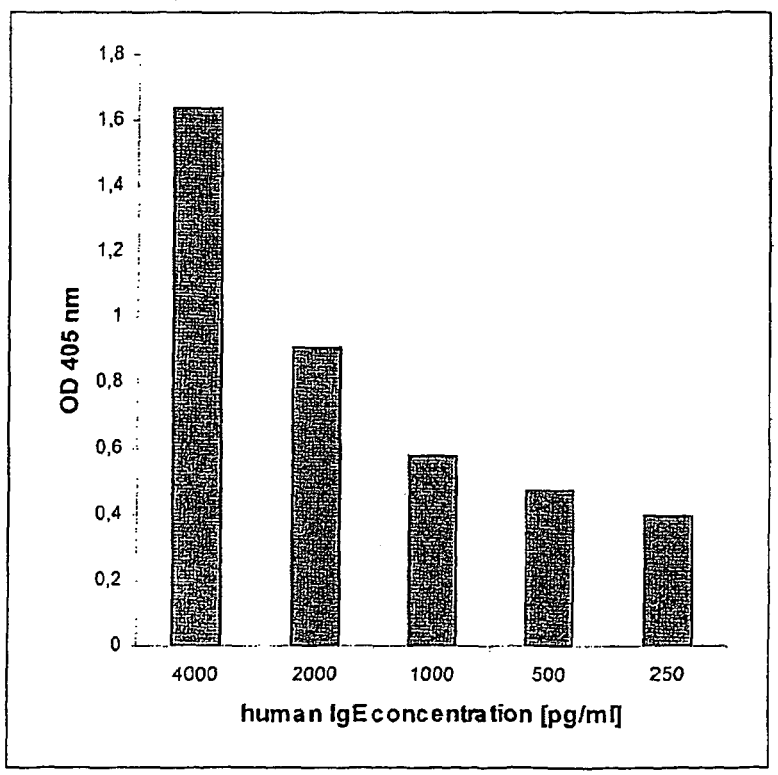

A

B

SEQUENCE LISTING

```
<160> NUMBER OF SEQ ID NOS: 35

<210> SEQ ID NO 1
<211> LENGTH: 38
<212> TYPE: DNA
<213> ORGANISM: Artificial Sequence
<220> FEATURE:
<223> OTHER INFORMATION: Primer

<400> SEQUENCE: 1
gatccgtacg tgtggggcag tccctcagaa acctaagg                              38

<210> SEQ ID NO 2
<211> LENGTH: 39
<212> TYPE: DNA
```

```
<213> ORGANISM: Artificial Sequence
<220> FEATURE:
<223> OTHER INFORMATION: Primer

<400> SEQUENCE: 2
gatcggcgcg cccggagctt ttattacagt aatgttgag                          39

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
accgaagtca tcgtctcctc                                               20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
cctcagtttg gcgtctaagc                                               20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gaggatcacg tcaagggatg                                               20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gcacccccaa tcctttattt                                               20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
accgaagtca tcgtctcctc                                               20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8 gcaccccaa tcctttattt                                                20
```

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
gatcggcgcg cccgcgagcc ccacatcgcc                               30

<210> SEQ ID NO 10
<211> LENGTH: 43
<212> TYPE: DNA
<213> ORGANISM: Artificial Sequence
<220> FEATURE:
<223> OTHER INFORMATION: Primer

<400> SEQUENCE: 10
gatctctaga tcagtgatgg tgatgtttac cagcctgttt ctg                43

<210> SEQ ID NO 11
<211> LENGTH: 28
<212> TYPE: DNA
<213> ORGANISM: Artificial Sequence
<220> FEATURE:
<223> OTHER INFORMATION: Primer

<400> SEQUENCE: 11
gatcggcgcg ccgcctgtag ccccagag                                 28

<210> SEQ ID NO 12
<211> LENGTH: 43
<212> TYPE: DNA
<213> ORGANISM: Artificial Sequence
<220> FEATURE:
<223> OTHER INFORMATION: Primer

<400> SEQUENCE: 12
gatctctaga tcagtgatgg tgatgtttac cagcctgttt ctg                43

<210> SEQ ID NO 13
<211> LENGTH: 28
<212> TYPE: DNA
<213> ORGANISM: Artificial Sequence
<220> FEATURE:
<223> OTHER INFORMATION: Primer

<400> SEQUENCE: 13
gatcggcgcg cccggcgctc agagctgc                                 28

<210> SEQ ID NO 14
<211> LENGTH: 43
<212> TYPE: DNA
<213> ORGANISM: Artificial Sequence
<220> FEATURE:
<223> OTHER INFORMATION: Primer

<400> SEQUENCE: 14
gatctctaga tcagtgatgg tgatgtttac cagcctgttt ctg                43

<210> SEQ ID NO 15
<211> LENGTH: 30
<212> TYPE: DNA
<213> ORGANISM: Artificial Sequence
<220> FEATURE:
<223> OTHER INFORMATION: Primer -continued

<400> SEQUENCE: 15
gatcggcgcg cccgcgagcc ccacatcgcc    30

<210> SEQ ID NO 16
<211> LENGTH: 52
<212> TYPE: DNA
<213> ORGANISM: Artificial Sequence
<220> FEATURE:
<223> OTHER INFORMATION: Primer

<400> SEQUENCE: 16
gatctctaga tcagtgatgg tgatggaact ccgggcatcc cttgacgtga tc    52

<210> SEQ ID NO 17
<211> LENGTH: 28
<212> TYPE: DNA
<213> ORGANISM: Artificial Sequence
<220> FEATURE:
<223> OTHER INFORMATION: Primer

<400> SEQUENCE: 17
gatcggcgcg ccgcctgtag ccccagag    28

<210> SEQ ID NO 18
<211> LENGTH: 52
<212> TYPE: DNA
<213> ORGANISM: Artificial Sequence
<220> FEATURE:
<223> OTHER INFORMATION: Primer

<400> SEQUENCE: 18
gatctctaga tcagtgatgg tgatggaact ccgggcatcc cttgacgtga tc    52

<210> SEQ ID NO 19
<211> LENGTH: 58
<212> TYPE: DNA
<213> ORGANISM: Artificial Sequence
<220> FEATURE:
<223> OTHER INFORMATION: Primer

<400> SEQUENCE: 19
gtacaagctt gctagcaaga tggaatcaca gacccaggtc ctcatgtccc tgctgctc    58

<210> SEQ ID NO 20
<211> LENGTH: 54
<212> TYPE: DNA
<213> ORGANISM: Artificial Sequence
<220> FEATURE:
<223> OTHER INFORMATION: Primer

<400> SEQUENCE: 20
atgtccctgc tgctctggat ttctggtacc tgtggggtcc ctcagaaacc taag    54

<210> SEQ ID NO 21
<211> LENGTH: 32
<212> TYPE: DNA
<213> ORGANISM: Artificial Sequence
<220> FEATURE:
<223> OTHER INFORMATION: Primer

<400> SEQUENCE: 21
gatccgtacg tgtggggccg tgacgttgga cg    32

<210> SEQ ID NO 22
<211> LENGTH: 29
<212> TYPE: DNA

<213> ORGANISM: Artificial Sequence
<220> FEATURE:
<223> OTHER INFORMATION: Primer

<400> SEQUENCE: 22
gatcggcgcg ccacctagga cggtcaggg                                      29

<210> SEQ ID NO 23
<211> LENGTH: 40
<212> TYPE: DNA
<213> ORGANISM: Artificial Sequence
<220> FEATURE:
<223> OTHER INFORMATION: Primer

<400> SEQUENCE: 23
ggtcctccaa gaacacttcc agggcaccta cagcgccagc                          40

<210> SEQ ID NO 24
<211> LENGTH: 40
<212> TYPE: DNA
<213> ORGANISM: Artificial Sequence
<220> FEATURE:
<223> OTHER INFORMATION: Primer

<400> SEQUENCE: 24
gctggcgctg taggtgccct ggaagtgtcc ttggaggacc                          40

<210> SEQ ID NO 25
<211> LENGTH: 38
<212> TYPE: DNA
<213> ORGANISM: Artificial Sequence
<220> FEATURE:
<223> OTHER INFORMATION: Primer

<400> SEQUENCE: 25
gcctgagcag ccgcgtccag gtcagcggca ccgattgg                            38

<210> SEQ ID NO 26
<211> LENGTH: 38
<212> TYPE: DNA
<213> ORGANISM: Artificial Sequence
<220> FEATURE:
<223> OTHER INFORMATION: Primer

<400> SEQUENCE: 26
ccaatcggtg ccgctgacct ggacgcggct gctcaggc                            38

<210> SEQ ID NO 27
<211> LENGTH: 31
<212> TYPE: DNA
<213> ORGANISM: Artificial Sequence
<220> FEATURE:
<223> OTHER INFORMATION: Primer

<400> SEQUENCE: 27
gatccatatg gcagtccctc agaaacctaa g                                   31

<210> SEQ ID NO 28
<211> LENGTH: 39
<212> TYPE: DNA
<213> ORGANISM: Artificial Sequence
<220> FEATURE:
<223> OTHER INFORMATION: Primer

<400> SEQUENCE: 28
gatcgcggcc gccggagctt ttattacagt aatgttgag                           39

<210> SEQ ID NO 29
<211> LENGTH: 774
<212> TYPE: DNA
<213> ORGANISM: Homo sapiens
<220> FEATURE:
<221> NAME/KEY: CDS
<222> LOCATION: (1)..(774)
<223> OTHER INFORMATION: Fc epsilon receptor alpha subunit coding region
<220> FEATURE:
<221> NAME/KEY: misc_feature
<222> LOCATION: (76)..(594)
<223> OTHER INFORMATION: Extracellular domain

<400> SEQUENCE: 29

```
atg gct cct gcc atg gaa tcc cct act cta ctg tgt gta gcc tta ctg        48
Met Ala Pro Ala Met Glu Ser Pro Thr Leu Leu Cys Val Ala Leu Leu
1               5                   10                  15 ttc ttc gct cca gat ggc gtg tta gca gtc cct cag aaa cct aag gtc        96
Phe Phe Ala Pro Asp Gly Val Leu Ala Val Pro Gln Lys Pro Lys Val
                20                  25                  30 tcc ttg aac cct cca tgg aat aga ata ttt aaa gga gag aat gtg act       144
Ser Leu Asn Pro Pro Trp Asn Arg Ile Phe Lys Gly Glu Asn Val Thr
            35                  40                  45 ctt aca tgt aat ggg aac aat ttc ttt gaa gtc agt tcc acc aaa tgg       192
Leu Thr Cys Asn Gly Asn Asn Phe Phe Glu Val Ser Ser Thr Lys Trp
        50                  55                  60 ttc cac aat ggc agc ctt tca gaa gag aca aat tca agt ttg aat att       240
Phe His Asn Gly Ser Leu Ser Glu Glu Thr Asn Ser Ser Leu Asn Ile
65                  70                  75                  80 gtg aat gcc aaa ttt gaa gac agt gga gaa tac aaa tgt cag cac caa       288
Val Asn Ala Lys Phe Glu Asp Ser Gly Glu Tyr Lys Cys Gln His Gln
                85                  90                  95 caa gtt aat gag agt gaa cct gtg tac ctg gaa gtc ttc agt gac tgg       336
Gln Val Asn Glu Ser Glu Pro Val Tyr Leu Glu Val Phe Ser Asp Trp
            100                 105                 110 ctg ctc ctt cag gcc tct gct gag gtg gtg atg gag ggc cag ccc ctc       384
Leu Leu Leu Gln Ala Ser Ala Glu Val Val Met Glu Gly Gln Pro Leu
        115                 120                 125 ttc ctc agg tgc cat ggt tgg agg aac tgg gat gtg tac aag gtg atc       432
Phe Leu Arg Cys His Gly Trp Arg Asn Trp Asp Val Tyr Lys Val Ile
130                 135                 140 tat tat aag gat ggt gaa gct ctc aag tac tgg tat gag aac cac aac       480
Tyr Tyr Lys Asp Gly Glu Ala Leu Lys Tyr Trp Tyr Glu Asn His Asn
145                 150                 155                 160 atc tcc att aca aat gcc aca gtt gaa gac agt gga acc tac tac tgt       528
Ile Ser Ile Thr Asn Ala Thr Val Glu Asp Ser Gly Thr Tyr Tyr Cys
                165                 170                 175 acg ggc aaa gtg tgg cag ctg gac tat gag tct gag ccc ctc aac att       576
Thr Gly Lys Val Trp Gln Leu Asp Tyr Glu Ser Glu Pro Leu Asn Ile
            180                 185                 190 act gta ata aaa gct ccg cgt gag aag tac tgg cta caa ttt ttt atc       624
Thr Val Ile Lys Ala Pro Arg Glu Lys Tyr Trp Leu Gln Phe Phe Ile
        195                 200                 205 cca ttg ttg gtg gtg att ctg ttt gct gtg gac aca gga tta ttt atc       672
Pro Leu Leu Val Val Ile Leu Phe Ala Val Asp Thr Gly Leu Phe Ile
210                 215                 220 tca act cag cag cag gtc aca ttt ctc ttg aag att aag aga acc agg       720
Ser Thr Gln Gln Gln Val Thr Phe Leu Leu Lys Ile Lys Arg Thr Arg
225                 230                 235                 240 aaa ggc ttc aga ctt ctg aac cca cat cct aag cca aac ccc aaa aac       768
Lys Gly Phe Arg Leu Leu Asn Pro His Pro Lys Pro Asn Pro Lys Asn
                245                 250                 255
```

```
aac tga                                                              774
Asn
```

<210> SEQ ID NO 30
<211> LENGTH: 257
<212> TYPE: PRT
<213> ORGANISM: Homo sapiens

<400> SEQUENCE: 30

```
Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Lys Val
            20                  25                  30

Ser Leu Asn Pro Pro Trp Asn Arg Ile Phe Lys Gly Glu Asn Val Thr
        35                  40                  45

Leu Thr Cys Asn Gly Asn Asn Phe Phe Glu Val Ser Ser Thr Lys Trp
    50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Leu Gln Phe Phe Ile
        195                 200                 205

Pro Leu Leu Val Val Ile Leu Phe Ala Val Asp Thr Gly Leu Phe Ile
    210                 215                 220

Ser Thr Gln Gln Gln Val Thr Phe Leu Leu Lys Ile Lys Arg Thr Arg
225                 230                 235                 240

Lys Gly Phe Arg Leu Leu Asn Pro His Pro Lys Pro Asn Pro Lys Asn
                245                 250                 255

Asn
```

<210> SEQ ID NO 31
<211> LENGTH: 519
<212> TYPE: DNA
<213> ORGANISM: Homo sapiens
<220> FEATURE:
<221> NAME/KEY: CDS
<222> LOCATION: (1)..(519)
<223> OTHER INFORMATION: Fc epsilon receptor alpha subunit coding
      region: extracellular domain

<400> SEQUENCE: 31

```
gtc cct cag aaa cct aag gtc tcc ttg aac cct cca tgg aat aga ata    48
Val Pro Gln Lys Pro Lys Val Ser Leu Asn Pro Pro Trp Asn Arg Ile
1               5                   10                  15 ttt aaa gga gag aat gtg act ctt aca tgt aat ggg aac aat ttc ttt    96
Phe Lys Gly Glu Asn Val Thr Leu Thr Cys Asn Gly Asn Asn Phe Phe
```

```
                  20                   25                   30
gaa gtc agt tcc acc aaa tgg ttc cac aat ggc agc ctt tca gaa gag      144
Glu Val Ser Ser Thr Lys Trp Phe His Asn Gly Ser Leu Ser Glu Glu
         35                   40                   45 aca aat tca agt ttg aat att gtg aat gcc aaa ttt gaa gac agt gga      192
Thr Asn Ser Ser Leu Asn Ile Val Asn Ala Lys Phe Glu Asp Ser Gly
 50                   55                   60 gaa tac aaa tgt cag cac caa caa gtt aat gag agt gaa cct gtg tac      240
Glu Tyr Lys Cys Gln His Gln Gln Val Asn Glu Ser Glu Pro Val Tyr
 65                   70                   75                   80 ctg gaa gtc ttc agt gac tgg ctg ctc ctt cag gcc tct gct gag gtg      288
Leu Glu Val Phe Ser Asp Trp Leu Leu Leu Gln Ala Ser Ala Glu Val
                 85                   90                   95 gtg atg gag ggc cag ccc ctc ttc ctc agg tgc cat ggt tgg agg aac      336
Val Met Glu Gly Gln Pro Leu Phe Leu Arg Cys His Gly Trp Arg Asn
            100                  105                  110 tgg gat gtg tac aag gtg atc tat tat aag gat ggt gaa gct ctc aag      384
Trp Asp Val Tyr Lys Val Ile Tyr Tyr Lys Asp Gly Glu Ala Leu Lys
        115                  120                  125 tac tgg tat gag aac cac aac atc tcc att aca aat gcc aca gtt gaa      432
Tyr Trp Tyr Glu Asn His Asn Ile Ser Ile Thr Asn Ala Thr Val Glu
130                  135                  140 gac agt gga acc tac tac tgt acg ggc aaa gtg tgg cag ctg gac tat      480
Asp Ser Gly Thr Tyr Tyr Cys Thr Gly Lys Val Trp Gln Leu Asp Tyr
145                  150                  155                  160 gag tct gag ccc ctc aac att act gta ata aaa gct ccg                  519
Glu Ser Glu Pro Leu Asn Ile Thr Val Ile Lys Ala Pro
                 165                  170

<210> SEQ ID NO 32
<211> LENGTH: 173
<212> TYPE: PRT
<213> ORGANISM: Homo sapiens

<400> SEQUENCE: 32

Val Pro Gln Lys Pro Lys Val Ser Leu Asn Pro Pro Trp Asn Arg Ile
  1               5                  10                  15

Phe Lys Gly Glu Asn Val Thr Leu Thr Cys Asn Gly Asn Asn Phe Phe
             20                  25                  30

Glu Val Ser Ser Thr Lys Trp Phe His Asn Gly Ser Leu Ser Glu Glu
         35                  40                  45

Thr Asn Ser Ser Leu Asn Ile Val Asn Ala Lys Phe Glu Asp Ser Gly
 50                  55                  60

Glu Tyr Lys Cys Gln His Gln Gln Val Asn Glu Ser Glu Pro Val Tyr
 65                  70                  75                  80

Leu Glu Val Phe Ser Asp Trp Leu Leu Leu Gln Ala Ser Ala Glu Val
                 85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
        115                 120                 125

Tyr Trp Tyr Glu Asn His Asn Ile Ser Ile Thr Asn Ala Thr Val Glu
130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro
                165                 170
```

<210> SEQ ID NO 33
<211> LENGTH: 1282
<212> TYPE: DNA
<213> ORGANISM: Chicken
<220> FEATURE:
<221> NAME/KEY: misc_feature
<222> LOCATION: (1)..(1282)
<223> OTHER INFORMATION: upsilon heavy chain constant region coding region

<400> SEQUENCE: 33

```
cgcgagcccc acatcgcccc cccgattgta ccctctatcc gcctgttgtt ccgactcggc        60
tgtcccgccg ccgtgggct gcctgttgtc cccttcgtcc gccggcggca tctcctggga       120
gggctccgga ggtacggcgg tggccggcag agtttcgggg accccgtga agctcagctt       180
cgtccgcctc agcccggcg agaagaggaa aagcttcgtc tgcagcgccg ccccggggg       240
ggcgctgctc aaaaaggagg tgcaggtctg ccgggtagat cccgtaccgc ctgtagcccc       300
agaggtgcag gtcctccacc cctcctcctg caccccgagc caatccgagt cggtggagct       360
gttgtgtttg gtgacgggt tctccccggc gtcggcggag gtcgaatggt tggtggacgg       420
agtggggga cttttggtgg cctcccaaag cccggcggtc cgcagcggat ccacctacag       480
cctgagcagc gcgtcaacg tcagcggcac cgattggagg aagggaaga gttacagctg       540
tagggtgagg cacccccgcaa ccaacaccgt ggtggaggat cacgtcaagg gatgcccgga       600
cggcgctcag agctgcagcc ccatccagct gtacgccatc ccacccagcc cgggcgagct       660
gtacatcagc ttagacgcca aactgaggtg cctggtggtc aacctgccca gcgattccag       720
cctcagcgtc acctggacca gggagaagag tgggaacctc cggcccgacc cgatggtcct       780
ccaagaacac ttcaacggca cctacagcgc cagcagcgcc gtcccccgtca gcacccagga       840
ttggttatcc ggggagaggt tcacctgcac cgtgcagcac gaggagctgc ccctgccgct       900
cagcaagagc gtctacagga cacgggaccc caccacccca cctctgatct accccttcgc       960
cccccacccg gaagagctgt ccctctcccg cgtcaccctg agctgcctgg tccgcggctt      1020
ccgcccacgt gacatcgaga tccggtggct ccgcgaccac cgcgccgttc cgccaccga      1080
attcgtcacc accgccgtcc tcccggaaga gagaaccgca aacggcgccg gcggtgacgg      1140
cgacaccttc ttcgtgtaca gtaagatgag cgtggagacc gccaagtgga acggcgggac      1200
ggtgttcgcc tgcatggcgg tgcacgaggc gctgcccatg cgcttcagcc agcgcacgct      1260
gcagaaacag gctggtaaat aa                                              1282
```

<210> SEQ ID NO 34
<211> LENGTH: 1821
<212> TYPE: DNA
<213> ORGANISM: Artificial
<220> FEATURE:
<223> OTHER INFORMATION: human/avian
<220> FEATURE:
<221> NAME/KEY: CDS
<222> LOCATION: (1)..(1821)
<223> OTHER INFORMATION: Chimera providing CH1-CH4 region

<400> SEQUENCE: 34

```
gtc cct cag aaa cct aag gtc tcc ttg aac cct cca tgg aat aga ata         48
Val Pro Gln Lys Pro Lys Val Ser Leu Asn Pro Pro Trp Asn Arg Ile
1               5                   10                  15 ttt aaa gga gag aat gtg act ctt aca tgt aat ggg aac aat ttc ttt         96
Phe Lys Gly Glu Asn Val Thr Leu Thr Cys Asn Gly Asn Asn Phe Phe
                20                  25                  30 gaa gtc agt tcc acc aaa tgg ttc cac aat ggc agc ctt tca gaa gag        144
Glu Val Ser Ser Thr Lys Trp Phe His Asn Gly Ser Leu Ser Glu Glu
```

-continued

```
                    35                  40                  45
aca aat tca agt ttg aat att gtg aat gcc aaa ttt gaa gac agt gga      192
Thr Asn Ser Ser Leu Asn Ile Val Asn Ala Lys Phe Glu Asp Ser Gly
 50                  55                  60 gaa tac aaa tgt cag cac caa caa gtt aat gag agt gaa cct gtg tac      240
Glu Tyr Lys Cys Gln His Gln Gln Val Asn Glu Ser Glu Pro Val Tyr
 65                  70                  75                  80 ctg gaa gtc ttc agt gac tgg ctg ctc ctt cag gcc tct gct gag gtg      288
Leu Glu Val Phe Ser Asp Trp Leu Leu Leu Gln Ala Ser Ala Glu Val
                     85                  90                  95 gtg atg gag ggc cag ccc ctc ttc ctc agg tgc cat ggt tgg agg aac      336
Val Met Glu Gly Gln Pro Leu Phe Leu Arg Cys His Gly Trp Arg Asn
                100                 105                 110 tgg gat gtg tac aag gtg atc tat tat aag gat ggt gaa gct ctc aag      384
Trp Asp Val Tyr Lys Val Ile Tyr Tyr Lys Asp Gly Glu Ala Leu Lys
            115                 120                 125 tac tgg tat gag aac cac aac atc tcc att aca aat gcc aca gtt gaa      432
Tyr Trp Tyr Glu Asn His Asn Ile Ser Ile Thr Asn Ala Thr Val Glu
        130                 135                 140 gac agt gga acc tac tac tgt acg ggc aaa gtg tgg cag ctg gac tat      480
Asp Ser Gly Thr Tyr Tyr Cys Thr Gly Lys Val Trp Gln Leu Asp Tyr
145                 150                 155                 160 gag tct gag ccc ctc aac att act gta ata aaa gct ccg ggc gcg ccc      528
Glu Ser Glu Pro Leu Asn Ile Thr Val Ile Lys Ala Pro Gly Ala Pro
                    165                 170                 175 gcg agc ccc aca tcg ccc ccc cga ttg tac cct cta tcc gcc tgt tgt      576
Ala Ser Pro Thr Ser Pro Pro Arg Leu Tyr Pro Leu Ser Ala Cys Cys
                180                 185                 190 tcc gac tcg gct gtc ccg ccg gcc gtg ggc tgc ctg ttg tcc cct tcg      624
Ser Asp Ser Ala Val Pro Pro Ala Val Gly Cys Leu Leu Ser Pro Ser
            195                 200                 205 tcc gcc ggc ggc atc tcc tgg gag ggc tcc gga ggt acg gcg gtg gcc      672
Ser Ala Gly Gly Ile Ser Trp Glu Gly Ser Gly Gly Thr Ala Val Ala
        210                 215                 220 ggc aga gtt tcg ggg acc ccc gtg aag ctc agc ttc gtc cgc ctc agc      720
Gly Arg Val Ser Gly Thr Pro Val Lys Leu Ser Phe Val Arg Leu Ser
225                 230                 235                 240 ccc ggc gag aag agg aaa agc ttc gtc tgc agc gcc gcc ccc ggg ggg      768
Pro Gly Glu Lys Arg Lys Ser Phe Val Cys Ser Ala Ala Pro Gly Gly
                    245                 250                 255 gcg ctc ctc aaa aag gag gtg cag gtc tgc cgg gta gat ccc gta ccg      816
Ala Leu Leu Lys Lys Glu Val Gln Val Cys Arg Val Asp Pro Val Pro
                260                 265                 270 cct gta gcc cca gag gtg cag gtc ctc cac ccc tcc tcc tgc acc ccg      864
Pro Val Ala Pro Glu Val Gln Val Leu His Pro Ser Ser Cys Thr Pro
            275                 280                 285 agc caa tcc gag tcg gtg gag ctg ttg tgt ttg gtg acg ggg ttc tcc      912
Ser Gln Ser Glu Ser Val Glu Leu Leu Cys Leu Val Thr Gly Phe Ser
        290                 295                 300 ccg gcg tcg gcg gag gtc gaa tgg ttg gtg gac gga gtg ggg gga ctt      960
Pro Ala Ser Ala Glu Val Glu Trp Leu Val Asp Gly Val Gly Gly Leu
305                 310                 315                 320 ttg gtg gcc tcc caa agc ccg gcg gtc cgc agc gga tcc acc tac agc     1008
Leu Val Ala Ser Gln Ser Pro Ala Val Arg Ser Gly Ser Thr Tyr Ser
                    325                 330                 335 ctg agc agc cgc gtc aac gtc agc ggc acc gat tgg agg gaa ggg aag     1056
Leu Ser Ser Arg Val Asn Val Ser Gly Thr Asp Trp Arg Glu Gly Lys
                340                 345                 350 agt tac agc tgt agg gtg agg cac ccc gca acc aac acc gtg gtg gag     1104
Ser Tyr Ser Cys Arg Val Arg His Pro Ala Thr Asn Thr Val Val Glu
```

```
                355                 360                 365
gat cac gtc aag gga tgc ccg gac ggc gct cag agc tgc agc ccc atc      1152
Asp His Val Lys Gly Cys Pro Asp Gly Ala Gln Ser Cys Ser Pro Ile
        370                 375                 380 cag ctg tac gcc atc cca ccc agc ccg ggc gag ctg tac atc agc tta      1200
Gln Leu Tyr Ala Ile Pro Pro Ser Pro Gly Glu Leu Tyr Ile Ser Leu
385                 390                 395                 400 gac gcc aaa ctg agg tgc ctg gtg gtc aac ctg ccc agc gat tcc agc      1248
Asp Ala Lys Leu Arg Cys Leu Val Val Asn Leu Pro Ser Asp Ser Ser
                405                 410                 415 ctc agc gtc acc tgg acc agg gag aag agt ggg aac ctc cgg ccc gac      1296
Leu Ser Val Thr Trp Thr Arg Glu Lys Ser Gly Asn Leu Arg Pro Asp
        420                 425                 430 ccg atg gtc ctc caa gaa cac ttc aac ggc acc tac agc gcc agc agc      1344
Pro Met Val Leu Gln Glu His Phe Asn Gly Thr Tyr Ser Ala Ser Ser
        435                 440                 445 gcc gtc ccc gtc agc acc cag gat tgg tta tcc ggg gag agg ttc acc      1392
Ala Val Pro Val Ser Thr Gln Asp Trp Leu Ser Gly Glu Arg Phe Thr
        450                 455                 460 tgc acc gtg cag cac gag gag ctg ccc ctg ccg ctc agc aag agc gtc      1440
Cys Thr Val Gln His Glu Glu Leu Pro Leu Pro Leu Ser Lys Ser Val
465                 470                 475                 480 tac agg aac acg gga ccc acc acc cca cct ctg atc tac ccc ttc gcc      1488
Tyr Arg Asn Thr Gly Pro Thr Thr Pro Pro Leu Ile Tyr Pro Phe Ala
                485                 490                 495 ccc cac ccg gaa gag ctg tcc ctc tcc cgc gtc acc ctg agc tgc ctg      1536
Pro His Pro Glu Glu Leu Ser Leu Ser Arg Val Thr Leu Ser Cys Leu
                500                 505                 510 gtc cgc ggc ttc cgc cca cgt gac atc gag atc cgg tgg ctc cgc gac      1584
Val Arg Gly Phe Arg Pro Arg Asp Ile Glu Ile Arg Trp Leu Arg Asp
        515                 520                 525 cac cgc gcc gtt ccc gcc acc gaa ttc gtc acc acc gcc gtc ctc ccg      1632
His Arg Ala Val Pro Ala Thr Glu Phe Val Thr Thr Ala Val Leu Pro
530                 535                 540 gaa gag aga acc gca aac ggc gcc ggc ggt gac ggc gac acc ttc ttc      1680
Glu Glu Arg Thr Ala Asn Gly Ala Gly Gly Asp Gly Asp Thr Phe Phe
545                 550                 555                 560 gtg tac agt aag atg agc gtg gag acc gcc aag tgg aac ggc ggg acg      1728
Val Tyr Ser Lys Met Ser Val Glu Thr Ala Lys Trp Asn Gly Gly Thr
                565                 570                 575 gtg ttc gcc tgc atg gcg gtg cac gag gcg ctg ccc atg cgc ttc agc      1776
Val Phe Ala Cys Met Ala Val His Glu Ala Leu Pro Met Arg Phe Ser
        580                 585                 590 cag cgc acg ctg cag aaa cag gct ggt aaa cat cac cat cac tga          1821
Gln Arg Thr Leu Gln Lys Gln Ala Gly Lys His His His His
        595                 600                 605

<210> SEQ ID NO 35
<211> LENGTH: 606
<212> TYPE: PRT
<213> ORGANISM: Artificial
<220> FEATURE:
<223> OTHER INFORMATION: Synthetic Construct

<400> SEQUENCE: 35

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
                20                  25                  30

Glu Val Ser Ser Thr Lys Trp Phe His Asn Gly Ser Leu Ser Glu Glu
        35                  40                  45
```

```
Thr Asn Ser Ser Leu Asn Ile Val Asn Ala Lys Phe Glu Asp Ser Gly
    50                  55                  60

Glu Tyr Lys Cys Gln His Gln Gln Val Asn Glu Ser Glu Pro Val Tyr
 65              70                  75                  80

Leu Glu Val Phe Ser Asp Trp Leu Leu Leu Gln Ala Ser Ala Glu Val
                 85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
            115                 120                 125

Tyr Trp Tyr Glu Asn His Asn Ile Ser Ile Thr Asn Ala Thr Val Glu
        130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Gly Ala Pro
                165                 170                 175

Ala Ser Pro Thr Ser Pro Pro Arg Leu Tyr Pro Leu Ser Ala Cys Cys
            180                 185                 190

Ser Asp Ser Ala Val Pro Pro Ala Val Gly Cys Leu Leu Ser Pro Ser
            195                 200                 205

Ser Ala Gly Gly Ile Ser Trp Glu Gly Ser Gly Thr Ala Val Ala
210                 215                 220

Gly Arg Val Ser Gly Thr Pro Val Lys Leu Ser Phe Val Arg Leu Ser
225                 230                 235                 240

Pro Gly Glu Lys Arg Lys Ser Phe Val Cys Ser Ala Ala Pro Gly Gly
                245                 250                 255

Ala Leu Leu Lys Lys Glu Val Gln Val Cys Arg Val Asp Pro Val Pro
            260                 265                 270

Pro Val Ala Pro Glu Val Gln Val Leu His Pro Ser Ser Cys Thr Pro
            275                 280                 285

Ser Gln Ser Glu Ser Val Glu Leu Leu Cys Leu Val Thr Gly Phe Ser
            290                 295                 300

Pro Ala Ser Ala Glu Val Glu Trp Leu Val Asp Gly Val Gly Gly Leu
305                 310                 315                 320

Leu Val Ala Ser Gln Ser Pro Ala Val Arg Ser Gly Ser Thr Tyr Ser
                325                 330                 335

Leu Ser Ser Arg Val Asn Val Ser Gly Thr Asp Trp Arg Glu Gly Lys
            340                 345                 350

Ser Tyr Ser Cys Arg Val Arg His Pro Ala Thr Asn Thr Val Val Glu
        355                 360                 365

Asp His Val Lys Gly Cys Pro Asp Gly Ala Gln Ser Cys Ser Pro Ile
        370                 375                 380

Gln Leu Tyr Ala Ile Pro Pro Ser Pro Gly Glu Leu Tyr Ile Ser Leu
385                 390                 395                 400

Asp Ala Lys Leu Arg Cys Leu Val Val Asn Leu Pro Ser Asp Ser Ser
                405                 410                 415

Leu Ser Val Thr Trp Thr Arg Glu Lys Ser Gly Asn Leu Arg Pro Asp
            420                 425                 430

Pro Met Val Leu Gln Glu His Phe Asn Gly Thr Tyr Ser Ala Ser Ser
            435                 440                 445

Ala Val Pro Val Ser Thr Gln Asp Trp Leu Ser Gly Glu Arg Phe Thr
450                 455                 460

Cys Thr Val Gln His Glu Glu Leu Pro Leu Pro Leu Ser Lys Ser Val
```

-continued

```
465                 470                 475                 480
Tyr Arg Asn Thr Gly Pro Thr Thr Pro Pro Leu Ile Tyr Pro Phe Ala
            485                 490                 495

Pro His Pro Glu Glu Leu Ser Leu Ser Arg Val Thr Leu Ser Cys Leu
            500                 505                 510

Val Arg Gly Phe Arg Pro Arg Asp Ile Glu Ile Arg Trp Leu Arg Asp
        515                 520                 525

His Arg Ala Val Pro Ala Thr Glu Phe Val Thr Thr Ala Val Leu Pro
    530                 535                 540

Glu Glu Arg Thr Ala Asn Gly Ala Gly Gly Asp Gly Asp Thr Phe Phe
545                 550                 555                 560

Val Tyr Ser Lys Met Ser Val Glu Thr Ala Lys Trp Asn Gly Gly Thr
            565                 570                 575

Val Phe Ala Cys Met Ala Val His Glu Ala Leu Pro Met Arg Phe Ser
            580                 585                 590

Gln Arg Thr Leu Gln Lys Gln Ala Gly Lys His His His His
            595                 600                 605
```

CHIMERA OF HUMAN IGE RECEPTOR α-CHAIN AND AVIAN CONSTANT IMMUNO-GLOBULIN DOMAINS FOR THE DETERMINATION OF SERUM IGE

CROSS REFERENCE TO RELATED APPLICATIONS

The present application claims priority to European Patent Application No. 0522582.0, filed Oct. 17, 2005, which is incorporated herein by reference in its entirety.

The instant application inter alia relates to chimeric fusion constructs comprising the extracellular portion of human FcεRIa and at least one avian constant immunoglobulin domain and the use thereof for in vitro diagnostic purposes.

BACKGROUND

More than 20% of the population suffer from type I allergic reactions. The prevalence of asthma, hay fever and other IgE-mediated diseases has increased dramatically in industrialized countries over the last decades, making allergies a very serious public health problem (Beasley et al., J Allergy Clin Immunol 105: 466-472, 2000).

For example, asthma prevalence rates increased by 75% in the United States between 1980 and 1994 (Doyle, Sci Am 282: 30, 2000).

The most important predisposing factor for the development of allergic diseases is atopy, the genetic predisposition to produce allergen-specific IgE. Childhood asthma is mainly found in patients who are atopic and sensitized to common environmental allergens including house dust mites, tree and grass pollens. Recent epidemiological studies suggest a close correlation between serum IgE levels and the presence or severity of asthma (Burrows et al., N Engl J Med 320: 271-277, 1989). In contrast, patients with a non-allergic asthma have negative skin tests to common allergens and normal total Ige serum levels. The association of increased IgE serum levels is also obvious for other allergic diseases such as seasonal allergic rhinitis, insect venom allergy or food allergies.

Symptoms of type I allergic reactions are due to the release of mediators (e.g. histamine) resulting from allergen-mediated crosslinking of IgE (immunoglobulin E) antibodies bound to IgE receptors on effector cells. The high-affinity IgE receptor FcεRI is mainly expressed on mast cells and basophils (Ravetch and Kinet, Ann Rev Immunol 9: 457, 1991), whereas the low-affinity IgE receptor FcεRII (CD23) is expressed on B cells (Conrad, Ann Rev Immunol 8: 623-645, 1990). Free serum IgE has a very short half-life of about two and a half days, while mast cells remain sensitized for up to 12 weeks following binding of IgE to high-affinity receptors.

Treatment modalities of type I allergies have substantially improved over the last decades. Allergen-specific immunotherapy (SIT) represents a curative approach. A rise in allergen-blocking IgG antibodies, particularly of the IgG4 class (Reid et al., J. Allergy Clin. Immunol. 78: 590-600, 1986), a reduction in the number of mast cells and eosinophils, and a decreased release of mediators (Varney et al., J. Clin. Invest. 92: 644-651, 1993) were found to be associated with successful SIT. However, for some patients including polysensitized and very young patients SIT is not applicable. The most advanced treatment modality that targets the pathophysiological cascade of allergen-mediated immune reactions earlier and in a more general way than SIT, is the inhibition of IgE responses by anti-IgE antibodies. The binding site of IgE for the high-affinity IgE receptor FcεRI is located within the third domain of the heavy chain, Cε3. A murine antibody, MAE1, was generated that recognizes the same residues in the Cε3 domain of IgE that are responsible for binding to FcεRI (Saban et al., J Allergy Clin Immunol 94: 836-843, 1994). To avoid sensitization to the murine antibody, a humanized version, containing 95% of a human IgG1 antibody and only 5% of the murine antibody, was constructed and named recombinant humanized monoclonal antibody (rhuMAb)-E25 (Presta et al., J Immunol 151: 2623-2632, 1993) or omalizumab (Xolair®). The main features of this anti-IgE antibody include a) recognition and binding to serum IgE, but not to IgG or IgA, b) inhibition of IgE binding to FcεRI, c) no binding to IgE bound to mast cells or basophils, thereby avoiding degranulation ('non-anaphylactic antibody'), and d) its capability to block mast cell degranulation upon passive sensitization in vitro or challenge with allergen in vivo. Treatment with omalizumab (Xolair®) also reduces the number of FcεRI receptors on basophils in atopic patients. Since omalizumab (Xolair®) binds to any IgE molecule irrespective of its allergen specificity, this therapeutic approach provides a valuable alternative to SIT. Recent clinical trial have demonstrated that anti-IgE is an effective agent for the therapy of allergies including moderate to severe allergic asthma and seasonal allergic rhinitis (Hamelmann et al., Allergy 57: 983-994, 2002; Hamelmann et al., Curr Opin Allergy Clin Immunol 3: 501-510, 2003).

In order to assess the success of anti-IgE treatment, methods for the in vitro measurement of IgE antibodies are required that allow differentiation between complexed and non-complexed serum IgE.

Currently available methods for the in vitro determination of serum IgE include the radio-allergosorbent test (RAST), various enzyme-linked immunosorbent assays (ELISA) and other IgE-binding techniques such as immunoelectrophoresis, immunoblot and immunodotblotting. RAST and ELISA assays are performed in three steps including immobilization of the standard/reference allergens on a solid phase (e.g., the well of a microtiter plate), binding of the IgE antibodies in the serum of a patient to the immobilized allergens, and determination of coupled IgE antibodies by labelled anti-IgE antibodies. All of these techniques, however, utilize for the detection of bound IgE polyclonal or monoclonal anti-IgE antibodies that are not capable of differentiating between complexed and non-complexed serum IgE. Since these antibodies recognize other epitopes than those residues in the Cε3 domain of IgE that are responsible for binding to FcεRI, free IgE as well as anti-IgE/IgE complexes are detected.

A new strategy for detecting allergen-specific antibodies in serum is the bead array technology. These multiplex assays can be performed in the flow cytometer or in any other similar analytical equipment that allows for the discrimination of different particles on the basis of size and color. The bead array technology employs a series of particles with discrete fluorescence intensities to simultaneously detect multiple soluble analytes from a single serum, plasma, or tissue fluid sample. The analytes can also be allergen-specific antibodies of the IgE subclass. For example, for the detection of allergen-specific antibodies specific capture beads carrying immobilized standard/reference allergens, are mixed with phycoerythrin-conjugated detection antibodies and are then incubated with test samples to form sandwich complexes. However, the polyclonal or monoclonal anti-IgE capture antibodies utilized for this technique are not suitable for the determination of non-complexed IgE due to the lack of specificity for the residues in the Cε3 domain of IgE that are responsible for binding to FcεRI.

In addition to solid-phase technology, fluid-phase systems have been established for the in vitro measurement of allergen-specific antibodies in serum. In these immunoassays, modified allergens are employed. The modified allergens contain one or more residues (e.g., biotin) that allow for subsequent binding of allergen-serum antibody complexes to a solid phase coated with a corresponding binding protein (e.g., streptavidin). The soluble polymer/copolymer support systems utilized in these assays, increase the number of binding sites and, thereby, the detection sensitivity. The most advanced fluid-phase assays for the detection of allergen-specific IgE antibodies utilize an enzyme-enhanced chemiluminescent enzyme immunoassay technique for the quantification of complexed specific antibodies. For example, for the detection of allergen-specific IgE antibodies, streptavidin-coated beads, biotinylated liquid allergens, and the patient's sample are incubated, and after a spin wash coupled IgE antibodies are detected with an alkaline phosphatase-labelled monoclonal anti-human IgE antibody using a chemiluminescent substrate (e.g., phosphate ester of adamantyl dioxetane). Again, the labelled monoclonal anti-human IgE antibody utilized for these fluid-phase systems detects free IgE as well as anti-IgE/IgE complexes.

One possibility to overcome these problems is the use of monoclonal antibodies with specificity for the residues in the C$\epsilon$3 domain of IgE that are responsible for binding to Fc$\epsilon$RI such as murine monoclonal antibody MAE1 or humanized monoclonal antibody E25 (omalizumab, Xolair®) as capture and/or detection antibody for the above listed IgE quantification procedures. However, the use of antibodies of mammalian origin raises a number of additional difficulties in practice due to the presence of rheumatoid factor (RF) and human anti-mouse IgG antibodies (HAMA) in serum samples. RF and HAMA are probably the most well known causes of false positive or false negative reactions in immunological assays (Boscato L M, Stuart M C, Clin Chem 34, 27-33, 1988). RF is an auto-antibody that reacts with the Fc part of IgG.

The disease most often associated with RF is rheumatoid arthritis, but RF can be found in serum from patients with many other diseases and also in 3-5% of healthy blood donors (Johnson P M, Faulk W P, Clin Immunol Immunopathol 6, 414-430, 1976). Production of HAMA is mainly the result of therapeutic approaches with mouse monoclonal antibodies, but HAMA may also be found in serum from patients who have not been treated with antibodies. RF or HAMA may react with both the capture antibody and the detection antibody in a sandwich assay, thereby mimicking antigen activity. A reaction with the detection antibody results in formation of an immune complex which may influence the activity of the detection antibody. HAMA may also react with the antigen-binding region of the detection antibody, thereby impairing or inhibiting antigen binding. The problem of RF and HAMA interference will increase as the sensitivity of the assay increases. Interference by anti-IgG antibodies and antibody-binding substances have been demonstrated in approximately 40% of serum samples from healthy individuals in an immunoradiometric assay (Boscato L, Stuart M, Clin Chem 32, 1491-1495; 1986). The prevalence of human anti-mammalian antibodies causing potential interferences in immunological assays varies from 1-80% in the general population (Kricka L J, Clin. Chem. 45, 942-956, 1999).

Furthermore, some mammalian IgG antibodies bound to a solid phase as well as antigen-antibody complexes comprising such antibodies, can activate the human complement system (Larsson A, Sjoquist J, J Immunol Methods 119, 103-109, 1989). Activated C4 molecules bind to the Fab region of IgG and may interfere with the antigen binding (Campbell R D, et al., Biochem J 189, 67-80, 1980). In clinical laboratories, most analyses are performed on serum samples. A newly obtained serum sample contains active complement, but the activity declines during storage and handling. Accordingly, the complement activity may vary between different patients and also between different samples from the same patient. To avoid activation of the complement cascade, EDTA is often included in tubes used for blood sampling.

EDTA prevents complement activation and coagulation by sequestering calcium ions. Most of the standards and controls used have been stored and contain an inactive complement system. This difference in activity between the samples and the standards will cause erroneous results. Complement activation was shown to interfere in an immunometric TSH assay and depressed the TSH values by up to 40% (Kapyaho K, et al., Scand J Clin Lab Invest 49, 211215, 1989).

In principle, the above mentioned problems, e.g. cross-reactivity and complement activation, could be avoided by using mammalian antibody fragments instead of complete antibodies. For example, IgG antibodies can be enzymatically cut by papain into Fab fragments (fragment antigen binding) and Fc fragments (fragment cristallizable). Furthermore, recombinant production of Fab fragments is possible. In a preferred form, light and heavy chain domains are formed by a single peptide chain, which can be recombinantly generated (scFv, single chain fragment variable). Libraries of scFv, in particular as phage display libraries, are available in the art, which facilitate generation of recombinant antibodies or scFv specific for a given antigen. One major limitation of scFv or Fab molecules, however, is their monovalent format, impairing the affinity of these molecules and, thereby, their applicability for analytical applications. Alternatively, bivalent $Fab_2$ fragments could be used, which still contain the hinge region, wherein the two heavy chains are connected by a disulfide linkage. $Fab_2$ can be produced by enzymatic digestion of antibodies with pepsin. However, especially for analytical applications, another major limitation of scFv, Fab and $Fab_2$ molecules is the lacking Fc region of the heavy chain. As a result, recognition of theses antibody fragments by secondary antibodies to the Fc region is severely impaired.

As an alternative to the above listed assay systems, basophil granulocytes have been used for the detection of allergen-specific antibodies in serum. Blood basophils together with submucosal mast cells are primary effector cells in IgE-mediated immediate-type allergic reactions such as allergic rhinitis, allergic asthma, IgE-mediated urticaria or anaphylactic shock.

The principle of the method is to challenge sensitized basophils, believed to be sensitized analogously to skin mast cells, with allergen which will cross-link surface-bound specific IgE causing histamine to be released from the cells (in vitro mediator release assay; MRA). Released histamine is determined and a dose-response curve can be constructed. In order to ensure that the basophils are responding properly, anti-IgE antibodies are applied as positive control, whereas the test substance is applied on basophils carrying no specific IgE to exclude non-specific histamine release. The histamine release tests have been shown to correlate well with other methods for in vitro measurement of allergen-specific antibodies in serum and with skin prick tests (Østergaard et al., Allergy 45: 231, 1990). More recently, the synthesis and release of leukotrienes has been applied to monitor the response of basophils upon allergen stimulation. While this assay is suitable for the detection of allergen-specific antibodies in serum, the level of free IgE in serum cannot be determined with sensitized basophils since the binding sites of their Fc$\epsilon$ receptors are already occupied.

Basophils could be used for the determination of free IgE in serum after stripping of their original IgE by a brief treatment at low pH (Pruzansky et al., J. Immunol. 131: 1949, 1983). The stripping step, however, can interfere with the biological function of these cells, which is likely to affect the reliability of the assay. Cord blood basophils which do not require the stripping step represent an alternative, but these cells are difficult to obtain. In principle, basophil cell lines such as the KU812 (Hara et al., Biochem. Biophys. Res. Commun. 247: 542, 1998) or animal cell lines transfected with the human FcεRI (Lowe et al., J. Immunol. Methods 184: 113, 1995) may be used as recipient cells for MRAs.

However, all cell-based assay systems pose important limitations for routine analyses since they are expensive, labor intensive, and difficult to standardize.

Application of a soluble derivative of the alpha chain of human FcεRI, also referred to as FcεRIα, as capture and/or detection reagent provides another possibility for establishing an IgE assay that allows differentiation between complexed and non-complexed serum IgE. The alpha chain of FcεRI binds IgE molecules with high affinity ($K_D$ of about $10^{-9}$ to $10^{-10}$ M). Prior investigators have disclosed the nucleic acid sequence for human FcεRIα as well as for a soluble fragment thereof (U.S. Pat. No. 4,962,035, by Leder et al.; U.S. Pat. No. 5,639,660, by Kinet et al.). By introduction of a stop codon before the single C-terminal transmembrane anchor, a soluble FcεRIα fragment of 172 amino acid residues has been expressed that mediates high affinity binding of IgE (Blank et al., J Biol Chem 266, 2639-2646, 1991). The dissociation rate of bound IgE from this soluble truncated receptor was comparable to that of FcεRI on intact cells. The extracellular portion of the human FcεRIα protein contains two immunoglobulin-like domains ($D_1$ and $D_2$) which belong to the truncated C2 subtype of the immunoglobulin superfamily (Kinet, Annu Rev Immunol 17: 931-972, 1999). There are seven N-linked carbohydrate attachment sites in the human FcεRIα molecule. They are distributed about the front and back of the molecule, but are not found on top of the molecule (Garman et al., Annu Rev Immunol 17: 973-976, 1999). Glycosylation of FcεRIα affects the secretion and stability of the receptor, but is not required for IgE-binding (Blank et al., J Biol Chem 266: 2639-2646, 1991). However, the deglycosylated receptor has a tendency to form oligomers and aggregates in solution (Robertson, J Biol Chem 268: 12736-12743, 1993; Scarselli et al., FEBS Lett 329: 223-226, 1993; Letourner et al., J Biol Chem 270: 8249-8256, 1995). Apparently, the carbohydrates reduce the affinity of the receptor for itself, thus preventing premature aggregation on the cell surface.

The alpha chain of human FcεRI has been used for the detection of human IgE and IgE from other species including canine, feline, and equine IgE (WO 98/23964).

However, the molecular mass of the soluble truncated FcεRIα-construct (unglycosylated) is less than 20 kDa and immobilization or labelling of this small protein is likely to impair its capability as capture and detection reagent due to steric hindrance problems. IgE is a bulky ligand and high affinity binding to FcεRIα requires unrestricted interaction of all involved amino acid residues.

Steric hindrance problems can be minimized by fusion of FcεRIα With a protein suitable for immobilization and detection. Especially mammalian constant immunoglobulin domains are suitable for this purpose since a variety of established techniques are available for site-directed immobilization and detection of immunoglobulins by species-specific antibodies. The IgE binding capacity of FcεRIα is not affected by fusion to immunoglobulin domains. Using an ELISA format, chimeric molecules comprising the extracellular portion of human FcεRIα and constant domains of the heavy chain of human IgG1 have been demonstrated to bind efficiently to immobilized human IgE (Haak-Frendscho et al., J Immunol 151: 351-358, 1993). As described earlier, however, the presence of mammalian immunoglobulin domains in capture or detection reagents can lead to false positive or false negative reactions in immunological assays.

The person skilled in the art is therefore faced with the need of generating improved capture and/or detection reagents that allow differentiation between complexed and non-complexed serum IgE and avoid or minimize the above mentioned problems in the use of mammalian antibodies and fusion proteins comprising FcεRIα and constant immunoglobulin domains of mammalian origin.

SUMMARY OF THE INVENTION

This problem is solved by the subject matter of the claims. In particular, the present invention provides a chimeric fusion construct comprising the extracellular portion of human FcεRIα and at least one avian constant immunoglobulin domain, in particular, at least one IgY constant domain. The format of these constructs can be monomeric or homodimeric. The constructs are useful for the determination of the serum level of human IgE and, in particular, the level of non-complexed IgE in the presence of IgE/anti-IgE complexes which allows to assess the success of anti-IgE treatment.

The chimeric constructs allow to combine the advantageous properties of IgY constant domains with the IgE binding characteristics of human FcεRIα. Due to the phylogenetic difference between avian and mammalian proteins, constructs comprising IgY constant domains eliminate assay problems associated with cross-reactivity of secondary mammalian antibodies, RF, HAMA, and complement activation.

Additionally, the present invention provides a chimeric fusion construct comprising a non-glycosylated derivative of the extracellular portion of human FcεRIα and non-glycosylated avian IgY constant immunoglobulin domains. The absence of N-glycans guarantees a lack of interference by C-type lectins in analytical applications and, thereby, a higher degree of reliability.

In another embodiment of the present invention nucleic acid sequences and vectors encoding the FcεRIα constructs are provided, as well as mammalian and prokaryotic host cells transfected with these sequences.

FIGURES

FIG. 1: A: human FcεRIα subunit coding region: corresponding to SEQ ID NO: 29 (amino acid sequence: SEQ ID NO:30); the extracellular domain (corresponding to SEQ ID NOs:31 and 32) is shown on a grey background.

B: chicken upsilon heavy chain constant region coding region $C_H$1-4: SEQ ID NO:33 (domains of the heavy chain constant regions are defined according to a conserved domain architecture retrieval tool (Geer et al., 2002).

C: homodimeric FcεRIα construct comprising IgY constant domains $C_H1$-$C_H4$ coding region: corresponding to SEQ ID NO:34 (amino acid sequence: SEQ ID NO:35).

FIG. 2: Examples of homodimeric FcεRIα constructs comprising constant domains of avian origin. Asn308 and Asn407 provide N-glycosylation sites; ecd: extracellular domain.

Figure 3:
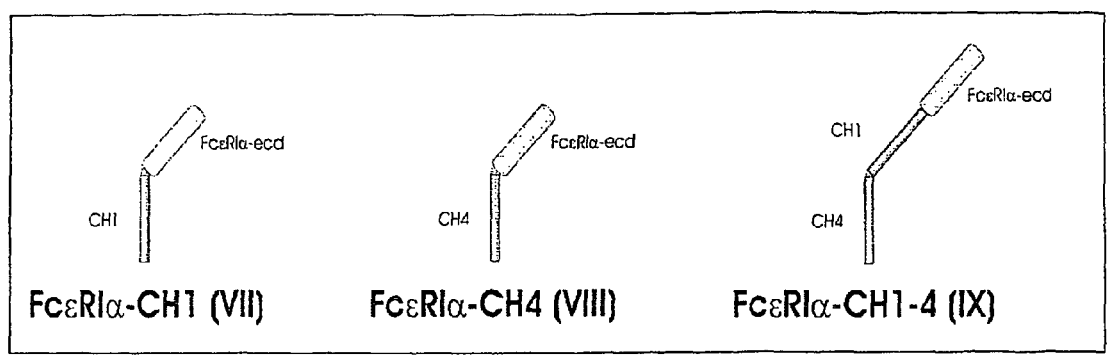

FIG. 3: Examples of monomeric FcεRIα constructs comprising constant domains of avian origin. ecd: extracellular domain.

Figure 4:
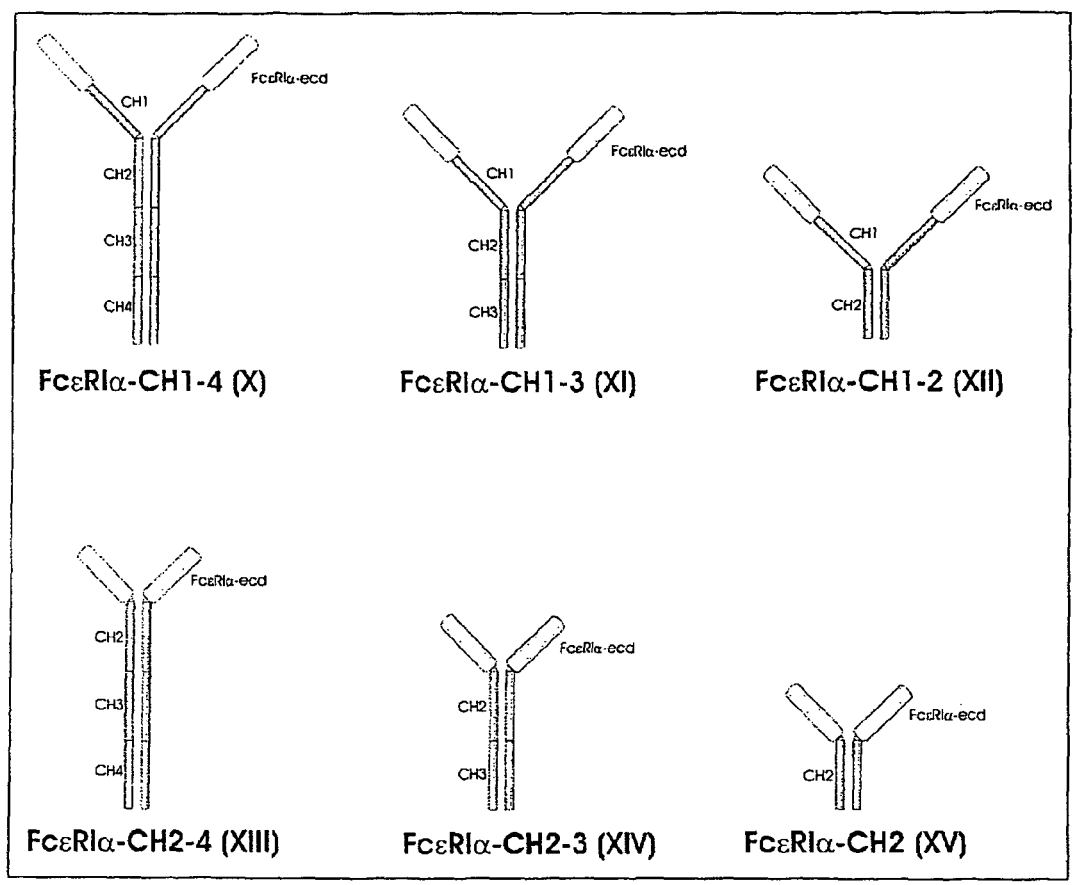

FIG. 4: Examples of FcεRIα constructs comprising non-glycosylated constant domains of avian origin. ecd: extracellular domain.

Figure 5:
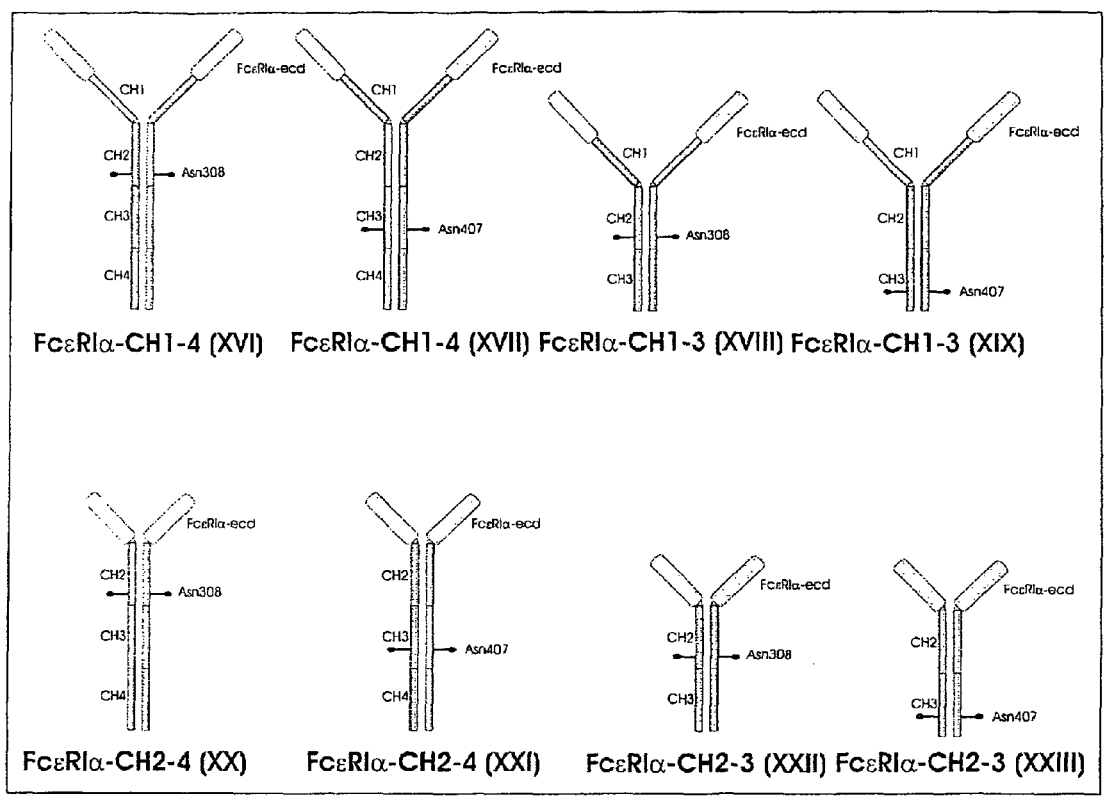

FIG. 5: Examples of FcεRIα constructs comprising monoglycosylated constant domains of avian origin. Asn308 and Asn407 provide N-glycosylation sites; ecd: extracellular domain.

Figure 6:
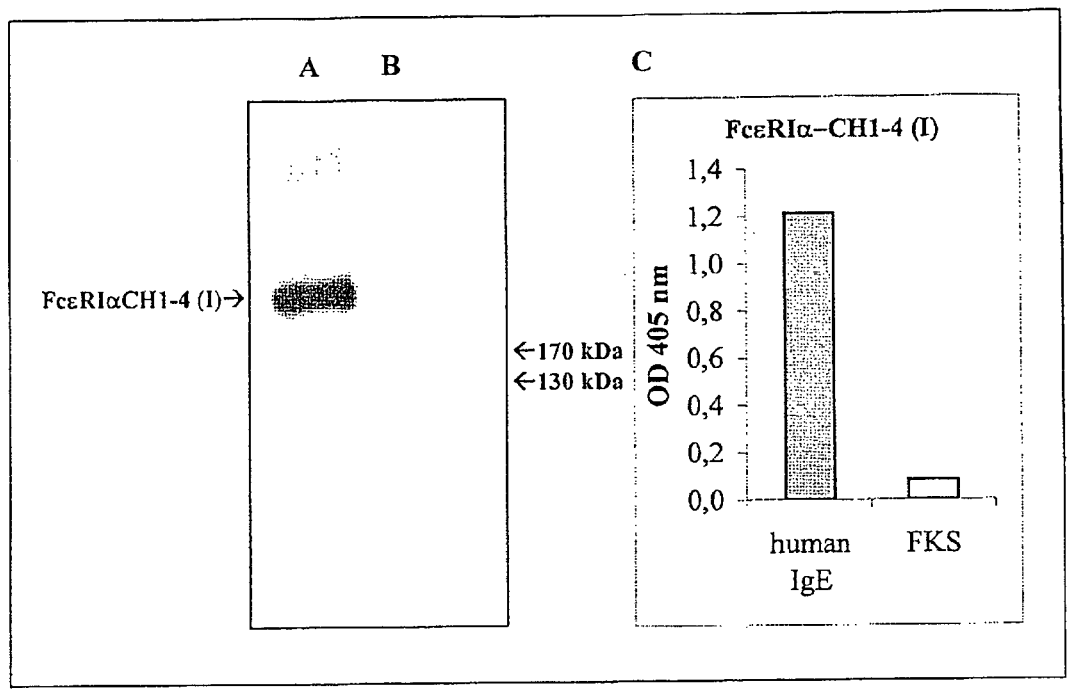

FIG. 6: Analysis of a homodimeric FcεRIα Construct comprising IgY constant domains $C_H1$-$C_H4$ by SDS-PAGE (A), immunoblot (B), and ELISA (C). After purification by Ni-NTA agarose chromatography, the construct was subjected to SDS-PAGE under non-reducing conditions followed by western blotting, and analyzed for IgE-binding by ELISA. For experimental details see examples 7 and 8.

FIG. 7: Assay principle for the determination of serum IgE using chimera of human FcεRIα and avian constant domains as capture reagent (left panel) or omalizumab as capture antibody (right panel). Detection of bound IgE is performed with polyclonal anti-human IgE or monoclonal anti-human IgE specific for an epitope of the human IgE molecule that is different from that of FcεRIα or omalizumab.

FIG. 8: Assay principle for the determination of non-complexed IgE in the presence of IgE/anti-IgE complexes using chimera of human FcεRIα and avian constant immunoglobulin domains as capture reagent.

FIG. 9: Concentration-dependent detection of recombinant human IgE using chimera of human FcεRIα and avian constant immunoglobulin domains CH1-4 as capture reagent. Detection of bound IgE was performed with polyclonal anti-human IgE (right panel) or monoclonal anti-human IgE specific for an epitope of the human IgE molecule that is different from that of FcεRIα (left panel).

FIG. 10: Concentration-dependent detection of human myeloma IgE using chimera of human FcεRIα and avian constant immunoglobulin domains CH1-4 as capture reagent (upper panel) or omalizumab as capture antibody (lower panel). Detection of bound IgE was performed with monoclonal anti-human IgE specific for an epitope of the human IgE molecule that is different from that of FcεRIα and omalizumab.

FIG. 11: Concentration-dependent detection of non-complexed human IgE in the presence of IgE/FcεRIα-construct-complexes using omalizumab as capture antibody. Detection of bound IgE was performed with monoclonal anti-human IgE specific for an epitope of the human IgE molecule that is different from that of FcεRIα and omalizumab.

FIG. 12: Concentration-dependent detection of non-complexed human IgE in the presence of IgE/anti-IgE (omalizumab)-complexes using omalizumab as capture antibody. Detection of bound IgE was performed with monoclonal anti-human IgE specific for an epitope of the human IgE molecule that is different from that of omalizumab.

FIG. 13: Quantitation of human IgE in the presence of IgE/anti-IgE-complexes using FcεRIα-$IgY_{CH1-4}$His as capture reagent. Detection of bound IgE was performed with monoclonal anti-human IgE specific for an epitope of the human IgE molecule that is different from that of FcεRIα and omalizumab.

A: Detection of Omalizumab-bound human IgE

B: Detection of human Myeloma IgE Standard

DETAILED DESCRIPTION OF THE INVENTION

The present invention relates to chimeric fusion constructs (also termed "chimeric antibody constructs" or "FcεRIα —IgY constructs", respectively) comprising the extracellular portion of human FcεRIα and at least one avian constant immunoglobulin domain, in particular, at least one IgY constant domain. The format of these constructs can be monomeric or homodimeric.

In the context of the present invention "extracellular portion of human FcεRIα" refers to sequences—both on nucleic acid and amino acid level—which correspond to or are derived from the sequences shown in FIG. 1. Specifically, the extracellular portion corresponds to the sequences represented as SEQ ID NO: 31 and SEQ ID NO:32 (which correspond to nucleotides 76-594 of SEQ ID NO:29 or amino acids 26 to 198 of SEQ ID NO:30). The invention also includes (artificial) modifications of the naturally occurring sequences of the extracellular portion of human FcεRIα, wherein these modified chimeric fusion constructs—on protein level—have the same or substantially the same binding properties as the non-modified chimeric fusion constructs.

Avian IgY, the equivalent of mammalian IgG, is the major low molecular weight serum immunoglobulin in oviparous (egg laying) animals. It is called IgY rather than IgG to distinguish it from its mammalian counterpart (Leslie G A, Clem L W, J Exp Med 130, 1337-1352, 1969). The overall structure of IgY is similar to mammalian IgG, with two light and two heavy chains. The light chain is lighter and the heavy chain of the IgY molecule is larger than its mammalian counterpart. The molecular mass has been reported to be approx. 167 kDa, slightly larger than IgG (approx. 160 kDa) (Sun S, et al., Rapid Commun Mass Spectrom 15, 708-712, 2001). The H chain (approx. 65 kDa), called upsilon (υ, capital letter Y) has one variable (V) region and four constant (C) regions. The light chain (approx. 18 kDa) is composed of one variable and one constant domain. In place of the hinge region of mammalian IgG, IgY has a more rigid structure, giving IgY limited flexibility. The Cυ3 and Cυ4 of the IgY are most closely related to the $C\gamma_2$ and $C\gamma_3$ of IgG, respectively, and the Cυ2 domain is absent in the γ-chain. The Cυ2 region was probably condensed to form the hinge region of IgG as studies have shown that IgY is an ancestor to mammalian IgG and IgE and also to IgA (Warr G W, et al., Immunol Today 16, 392-398, 1995).

An IgY constant domain in the context of the invention refers to an immunoglobulin domain that has a homology of at least 50%, preferably at least 70%, more preferably at least 80% or at least 90%, most preferred at least 95% amino acid homology to the corresponding IgY domain. Thus, e.g., one, two or three amino acids can be deleted, inserted or substituted. In particular, conservative substitutions are contemplated. The boundaries between the domains are preferably defined as by the conserved domain retrieval tool (Geer et al., 2002), however, they can also be shifted.

Due to the phylogenetic difference between avian IgY and mammalian IgG, human FcεRIα constructs comprising IgY constant domains provide several important advantages for analytical applications. One important advantage is the lack of cross-reactivity with mammalian antibodies. For example, utilizing polyclonal mammalian antibodies as secondary anti-IgE antibodies for the detection of captured human serum IgE, these antibodies can cross-react with mammalian capture antibodies. Because chicken IgY constant domains are so different from mammalian IgG constant domains, potential cross-reactivity of secondary mammalian anti-IgE antibodies can be minimized by using constructs of human FcεRIα and IgY constant domains as capture reagent.

Another advantage of the phylogenetic difference between avian and mammalian species is the lack of human complement activation by IgY antibodies. Because the constructs of the invention do not activate the human complement system, they can be used in analytical assays to reduce interference by complement activation (Larsson A, et al., J Immunol Methods 156, 79-83, 1992).

Still another important advantage of the phylogenetic difference between avian and mammalian species is the lack or minimisation of interaction of the construct of the invention with the rheumatoid factor (RF), human anti-mouse IgG antibodies (HAMA), and other anti-mammalian antibodies potentially present in human sera.

The IgY constant domains do not interact with RF or HAMA and can thus be used to avoid interference due to these factors (Larsson A, et al., Clin Chem 37, 411-414, 1991; Larsson A, Mellstedt H., Hybridoma 11, 33-39, 1992).

Thus, the phylogenetic difference of avian IgY antibodies to IgG antibodies of mammalian origin, and the use of IgY constant domains in the FcεRIα constructs of the invention provides several important advantages for analytical applications including the lack of cross-reactivity with mammalian antibodies, the lack of human complement activation, and the lack of interaction with human anti-mouse antibodies and the rheumatoid factor.

Preferred Constructs

In the context of the invention "FcεRIα-IgY construct" refers to constructs comprising the extracellular portion of human FcεRIα (see definition above) and at least one avian constant immunoglobulin domains, in particular, an IgY constant domain or a combination of IgY domains, which are capable of forming (homo)dimeric molecules (FIG. 2), and monomeric constructs comprising the extracellular portion of human FcεRIα and avian constant immunoglobulin domains, in particular, IgY constant domains that are not capable of forming dimeric molecules (FIG. 3).

A preferred construct of the instant invention has the sequence shown in SEQ ID NO: 35.

For homodimeric constructs, the IgY domain or a combination of IgY domains selected from the group consisting of $C_H1$, $C_H2$, $C_H3$, and $C_H4$ IgY domains, are capable of forming dimeric molecules. The construct can comprise one, two, three or four IgY constant domains. According to one embodiment, the IgY domain is a $C_H2$ constant domain. Preferably, the construct comprises a combination of IgY domains selected from the group consisting of (a) $C_H1$ and $C_H2$, (b) $C_H1$, $C_H2$ and $C_H3$, (c) $C_H1$, $C_H2$, $C_H3$ and $C_H4$, (d) $C_H2$ and $C_H3$, (e) $C_H2$, $C_H3$ and $C_H4$ IgY constant domains. Constructs comprising truncated IgY heavy chains provide a lower molecular mass than complete antibodies, which in many cases has been shown to be associated with increased expression rates. Instead of the conventional domains, fragments or variants thereof that do not inhibit folding or dimerisation of the constructs can be used. The boundaries between the domains, and thus the species origin of fragments at these boundaries can also be varied, as long as folding and dimerisation of the constructs is ensured.

In homodimeric constructs comprising the extracellular portion of human FcεRIα and the $C_H1$ and $C_H2$ IgY domains, or only the $C_H2$ IgY domain, the amino acids E and F are fused to the carboxyterminal end of the IgY $C_H2$-domain (3' boundary). Constructs lacking the $C_H3$ and $C_H4$ domains require a stop codon at the 3' boundary of the $C_H2$ domain.

While a crystal structure of IgY constant domains is not available, the crystal structure of constant domains of mammalian IgE which is known to be close to chicken IgY in terms of the number of $C_H$ domains, the number of exons and exon lengths as well as the organization of intradomain and interchain disulfide bonds (Warr G W, et al., Immunol. Today 16, 392-398, 1995), has been published recently (Wan T, et al., Nat. Immunol. 3, 681-686, 2002). The analysis revealed an asymmetrically bent conformation of IgE with the $C_H2$ domains forming highly bent structures at $C_H2$-$C_H3$ junctions. Therefore, truncation of mammalian IgE heavy chains at the $C_H2$ domain is considered likely to fundamentally impair the folding and assembly process of IgE. As a result of the close relationship of mammalian IgE and chicken IgY antibodies, similar considerations apply to IgY antibody constructs lacking the $C_H3$ and $C_H4$ domains. On the other hand, ducks express a truncated version of IgY lacking the $C_H3$ and $C_H4$ domains, but the $C_H2$ domain of this truncated duck antibody is followed by a terminal exon consisting of nucleic acids encoding EF and a stop codon. Utilizing single chain variable fragments (scFv) as model for the construction of FcεRIα-fusion proteins comprising the IgY $C_H2$-domain followed at its carboxyterminal end by the amino acids E and F, it could be demonstrated that such constructs are expressed as homodimeric molecules.

Constructs Comprising the Extracellular Fragment of Human FcεRIα and Mono-Glycosylated or Non-Glycosylated IgY Constant Domains Another limitation for analytical applications is the interaction of mammalian immunoglobulins and IgY antibodies via their oligosaccharide chains with C-type lectins in human sera and other human body fluids. C-type lectins bind sugars in a calcium-dependent manner via highly conserved carbohydrate recognition domains (CRD). C-Type lectins are either produced as transmembrane proteins, e.g., on dendritic cells and Langerhans cells (for a review, see Figdor C G, et al., Nature Rev. Immunol. 2, 77-84, 2002), or secreted as soluble proteins. Examples of soluble C-type lectins include the mannan-binding lectin (MBL), the surfactant protein A (SP-A) and D (SP-D), and the conglutenins CL-46 and CL-43, all of which belong to the collectin family (for a review, see Van de Wetering J K., et al., Eur. J. Biochem. 271, 1229-1249, 2004). MBL is secreted into the blood stream. The presence of substantial amounts of MBL in the small intestine suggests that this protein is acting as a humoral immune factor in the intestine, similar to secretory IgA. SP-A and SP-D are secreted at the luminal surface of pulmonary epithelial cells, and recently an increased expression of SP-D in the gastric mucosa during *Heliobacter pylori* infection has been reported, pointing to a role of the surfactant proteins in mucosal defense systems. The serum collectins conglutenin CL-46 and CL-43 have so far only be detected in bovidae, where the liver is their main site of production. The basic functional unit of collectins is a trimer, but the number of trimeric units per collectin molecule differs among the collectins. MBL and SP-A form octadecamers of six trimeric subunits, with their overall structure resembling a bouquet of flowers, whereas SP-D and the bovine conglutein proteins are assembled into dodecamers of four trimeric subunits. In addition, SP-D can form even higher-order multimers with a mass of several million kDa. The size of fully assembled collectins ranges from 13 nm for MBL to about 100 nm for SP-D. In order to recognize a variety of cell surface saccharides, collectins provide a broad monosaccharide specificity including mannose, galactose, and glucose.

Although the $K_d$ of the binding of a single CRD with a monosaccharide ligand is in the order of $10^{-3}$ M., the $K_d$ of binding of higher-order multimers of collectins to polyvalent ligands is in the order of $10^{-8}$ to $10^{-11}$ M. As a result, IgY and mammalian immunoglobulins can be bound tightly via their oligosaccharide chains by collectins. For example, MBL has been shown to bind agalactosylated glycoforms of IgG (Malhotra R., et al. Nat. Med. 1, 237-243, 1995) and to polymeric forms of serum IgA (Roos A., et al. J. Immunol. 167, 2861-2868, 2001). In chicken IgY, each H-chain contains two potential N-glycosylation sites located on CH2 (Asn308) and CH3 (Asn407) domains. The CH2 domain contains bitantennary complex-type N-glycans (neutral, 29.9%; monosialyl, 29.3%; disialyl, 3.7%), whereas the CH3 domain contains high-mannose-type oligosaccharides (monoglucosy-lated, 26.8%; others, 10.5%) (Suzuki N, Lee Y C, Glycobiology 14, 275-292, 2004). The structural properties of complex-type N-glycans from chicken IgY resemble those of human IgG (Suzuki N, et al., J. Biol. Chem. 278, 46293-46306, 2003). Both human IgG and chicken IgY possess biantennary complex-type oligosaccharides with and without core alpha 1-6 Fuc and/or bisecting GlcNAc. Both antibodies have a monogalactosylated branch predominantly on the GlcNAc beta 1-2 Man alpha 1-6 Man arm. Monosialylation in chicken IgY occurs on the Gal beta 1-4 GlcNAc beta 1-2 Man alpha 1-3 Man arm, which is also the case in normal human IgG (Takahashi N, et al., Anal. Biochem. 226, 139-146, 1995). Due to these similarities, N-glycans of IgY antibodies pose similar problems as those of human and other mammalian antibodies. In ELISA-type assays including those for the determination of free serum IgE, the presence of soluble C-type lectins in sera of patients can lead to false positive results as described for RF and HAMA (Boscato L M, Stuart M C, Clin Chem 34, 27-33, 1988). For example, monoclonal capture antibodies with specificity for human IgE produced by hybridoma technology or by expression in mammalian cells are glycoproteins which will bind soluble C-type lectins upon exposure to patient's sera. Since many C-type lectins such as MBL form oligomers of trimeric subunits, bound C-type lectins are likely to provide additional binding sites for glycosylated detection antibodies which could result in false positive data. Therefore, there is a need in the field for monoclonal antibodies or fragments thereof which do not interact with C-type lectins.

The present invention provides constructs comprising the extracellular portion of human FcεRIα and avian (IgY) constant immunoglobulin domains with one or more deleted glycosylation sites. Glycosylation of only one potential site on IgY constant domains reduces interference by C-type lectins in diagnostic and therapeutic applications, and is likely to help folding, assembling, and secreting such constructs in eukaryotic cells. One line of evidence for this assumption is the observation that glycosylation site Asn407 of IgY antibodies is well conserved in mammalian IgG (Asn297) and mammalian IgE (Asn394) although the number and position varies among the different species (Suzuki N, Lee Y C, Glycobiology 14, 275-292, 2004). Structural analyses of constant domains of mammalian IgE and IgG have demonstrated that N-glycans on Asn394 (mammalian IgE) and Asn297 (mammalian IgG) are buried in a cavity between the two heavy chains. Although the function of N-glycans in the cavity between the two heavy chains of mammalian IgE, IgG, and avian IgY remains to be elucidated, they probably play a role in folding, assembly, and stabilization of the immunoglobulin structures. Human IgE lacking N-glycosylation at Asn394 by point mutation has been reported to tend to self-aggregation (Basu M, et al., J. Biol. Chem. 268, 13118-13127, 1993), suggesting that N-glycans at this position are involved at least in stabilization of the protein structure by conferring suitable hydrophilicity to the cavity (Suzuki N, Lee Y C, Glycobiology 14, 275-292, 2004). Therefore, mono-glycosylation of IgY constant domains can be expected to help folding, assembling, and secreting such constructs in eukaryotic cells.

However, utilizing single chain variable fragments (scFv) as model for the construction of fusion proteins comprising avian constant domains, it has surprisingly been found that such constructs are correctly folded and secreted, even if both glycosylation sites are deleted. Therefore, in one embodiment the avian constant domains of the FcεRIα-fusion protein constructs are thus non-glycosylated. The absence of N-glycans guarantees a lack of interference by C-type lectins in IgE quantitation procedures. Compared to constructs comprising glycosylated IgY constant domains, constructs comprising non-glycosylated IgY constant domains provide a higher degree of reliability in diagnostic assay procedures.

Preferred constructs with non-glycosylated IgY constant domains include homodimeric constructs comprising the extracellular portion of human FcεRIα and avian constant immunoglobulin domains, in particular, IgY constant domains capable of forming dimeric molecules (FIG. 4), and monomeric constructs comprising the extracellular portion of human FcεRIα and avian constant immunoglobulin domains, in particular, IgY constant domains that are not capable of forming dimeric molecules.

Other preferred fusion protein formats of this part of the invention include constructs comprising the extracellular portion of human FcεRIα and mono-glycosylated avian constant immunoglobulin domains, in particular, mono-glycosylated IgY constant domains (FIG. 5). In mono-glycosylated constructs, IgY constant domains are glycosylated either on Asn308 (CH2 domain) or on Asn407 (CH3 domain).

Constructs Comprising Non-Glycosylated Derivatives of the Extracellular Fragment of Human FcεRIα and Non-Glycosylated IgY Constant Domains There are seven N-linked carbohydrate attachment sites in the human FcεRIα molecule and in the truncated extracellular fragment expressed in CHO cells, all seven sites proved to be glycosylated (Letourner et al., J Biol Chem 270: 8249-8256, 1995). Glycosylation of FcεRIα is not required for IgE-binding (Blank et al., J Biol Chem 266: 2639-2646, 1991), but mutations of the carbohydrate attachment sites had an additive effect on the folding and secretion. Mutation of all seven N-glycosylation sites resulted in misfolding and retention of the fragment in the endoplasmic reticulum (Letourner et al., J Biol Chem 270: 8249-8256, 1995). Tunicamycin treatment reduced the folding efficiency in CHO cells substantially, but small quantities of non-glycosylated FcεRIα were expressed (Blank et al., J Biol Chem 266: 2639-2646, 1991). These data indicate that glycosylation facilitates correct folding in eukaryotic cells, but is not absolutely required for secretion.

The instant invention thus also relates to antibody constructs, wherein one or more glycosylation site(s) of the extracellular portion of human FcεRIα is(are) deleted. In addition, of course, one or more glycosylation site(s) of the immunoglobulin domain(s) may be deleted. According to a preferred embodiment, both the extracellular portion of human FcεRIα and the immunoglobulin domain(s) are non-glycosylated.

A functional, non-glycosylated extracellular fragment of FcεRIα can be expressed in reasonable yields in *E. coli* (Robertson, J Biol Chem 268: 12736-12743, 1993; Letourner et al., J Biol Chem 270: 8249-8256, 1995). In contrast to non-glycosylated FcεRIα fragments expressed in mammalian cells, those expressed in *E. coli* do not show a tendency to form oligomers and aggregates. Therefore, prokaryotic expression appears to be most appropriate for the production of non-glycosylated FcεRIα fragments and chimeric constructs of the invention comprising non-glycosylated FcεRIα fragments and non-glycosylated IgY constant domains.

Preferred fusion protein formats of this part of the invention comprise a non-glycosylated derivative of the extracellular portion of human FcεRIα and non-glycosylated avian constant immunoglobulin domains selected from the group consisting of $C_H1$, $C_H2$, $C_H3$, and $C_H4$ IgY domains. The construct can comprise one, two, three or four IgY constant domains.

FcεRIα constructs comprising only one or two IgY constant domains provide a lower molecular mass, require less disulfide bond formation and, therefore, are associated with increased expression rates. Instead of the conventional domains, fragments or variants thereof that do not inhibit folding of the constructs can be used. The boundaries between the domains, and thus the species origin of fragments at these boundaries can also be varied, as long as folding of the constructs is ensured.

Nucleic Acids and Expression System

The present invention also provides nucleic acid sequences and vectors encoding the above listed constructs of the invention. The invention thus relates to nucleic acid molecules encoding the antibody constructs of the invention, as well as to expression vectors comprising said nucleic acid molecules under control of appropriate promoters. The expression vectors include procaryotic as well as eukaryotic expression vectors.

According to a preferred embodiment, the invention relates to a nucleic acid encoding the chimeric fusion construct having the amino acid sequence represented as SEQ ID NO:35. Specifically the nucleic acid encoding said homodimeric FcεRIα construct comprising IgY constant domains $C_H1$-$C_H4$ has the nucleic acid sequence shown as SEQ ID NO:34. In a particular embodiment, vectors are included, which comprise the aforementioned specific nucleic acid sequences.

To produce the constructs, one having ordinary skill in the art can prepare a DNA molecule encoding the construct using well known techniques. The coding sequence can be obtained from natural sources or synthesized or otherwise constructed using widely available starting materials by routine methods. In some embodiments, a DNA molecule that includes a nucleotide sequence that encodes a construct of the invention may be synthesized using the amino acid sequence information herein and the genetic code. When the coding DNA is prepared synthetically, advantage can be taken of known codon preferences of the intended host where the DNA is to be expressed. One having ordinary skill in the art can insert that DNA molecule into a commercially available expression vector for use in well known expression systems, employing well known methods and readily available starting materials (see e.g., Sambrook et al., Molecular Cloning. A Laboratory Manual, second ed., Cold Spring Harbor Press, 1989).

The present invention thus also relates to nucleic acid sequences and expression vectors comprising this nucleic acid molecule under control of an appropriate promoter. The potential glycosylation sites can be eliminated by site-directed mutation using well known techniques.

In another embodiment, the present invention provides expression systems suitable for the production of the above listed constructs. Homodimeric constructs and those comprising glycosylated components or those requiring complex disulfide bond formation, have to be expressed in eukaryotic systems which provide a variety of processing mechanisms in the endoplasmatic reticulum (ER), including chaperone-assisted folding, glycosylation and oxidation. Several eukaryotic hosts including commonly used yeast, fungal cells, insect cells, mammalian cells, and cells of higher plants, are available for the production of the construct of the invention. The particulars for the construction of expression systems suitable for the desired host are known to those in the art. As shown in FIG. 6, HEK cells proved to be capable of expressing and secreting the construct of the invention as an immunoreactive fusion protein. Thus, the present invention also relates to a method of expressing the construct of the invention comprising the extracellular portion of human FcεRIα and avian constant immunoglobulin domains, in eukaryotic cells.

The present invention provides also prokaryotic expression systems suitable for the production of non-glycosylated constructs. One advantage of prokaryotic systems is their ability to produce protein at low costs and in large quantities. Preferably, the expression is directed to the periplasmic space of Gram negative bacteria due to its oxidizing environment. The extracellular portion of human FcεRIα has been expressed as functional molecule in *E. coli* using the pel-B leader from the pectate lyase gene for directing secretion of the receptor fragment to the periplasmic space (Letourner et al., J Biol Chem 270: 8249-8256, 1995).

The same leader sequence has been utilized successfully for periplasmic expression of antibody fragments (for a review, see Verma et al., J Immunol Meth 216: 165-181, 1998). The particulars for the construction of expression systems suitable for the desired prokaryotic host are known to those in the art.

Analytical Applications

The construct of the invention can advantageously be used for in vitro diagnostic purposes, such as for the in vitro quantitation of human serum IgE, and in particular for the in vitro quantitation of non-complexed human serum IgE in the presence of IgE/anti-IgE complexes, wherein the monoclonal anti-IgE antibody specifically recognizes the residues in the Cε3 domain of IgE that are responsible for binding to FcεRI (e.g., murine monoclonal antibody MAE1 or humanized monoclonal antibody E25 designated omalizumab or Xolair®). Utilization of the construct of the invention for such applications minimizes cross-reactivity and false positive and negative results. Particular advantages are provided by use of those constructs that comprise a non-glycosylated fragment of human FcεRIα and non-glycosylated avian constant domains. Further applications are found as research tools or for biotechnological methods, e.g., in purification of IgE antibodies. The invention thus also provides a diagnostic agent or kit comprising the antibody construct disclosed herein.

In summary, the constructs of the invention offer great opportunities for diagnostic applications in atopic diseases.

The invention is described below by means of examples and figures, representing preferred embodiments of the invention, which however, shall not be considered to limit the invention.

EXAMPLES

A variety of constructs are suitable for the present invention. The structure of some of these formats described in the following examples are shown in FIGS. 2-5. Experimental methods were carried out following standard methods well known in the art (e.g., Sambrook J, Fritsch E F, Maniatis T. Molecular Cloning. A Laboratory Manual, second ed., Cold Spring Harbor Press, 1989).

Example 1

Amplification of the Extracellular Domain of Human IgE Receptor Alpha-Chain (FcεRIα-ecd)

The human FcεRIα extracellular domain (FcεRIα-ecd) was synthesized from cDNA derived from human peripheral mononuclear cells. FcεRIα-ecd was amplified using one PCR primer containing a Pfl23 II site (gatc cgtacg tgt ggg GCA GTC CCT CAG AAA CCT AAG G, SEQ ID NO:1) and another primer containing an Asc I site (gatc ggcgcgcc cggagcttttattacagtaatgttgag, SEQ ID NO:2). Utilizing Pwo-Polymerase (PeqLab, Germany) in combination with a mastercycler gradient (Eppendorf, Germany), following protocol was applied for PCR amplifications: 1×90 s 95° C., 30×(20 s 95° C., 1 min 60° C., 1 min 72° C.), 1×5 min 72° C.

Example 2

Amplification of IgY Constant Domains

All IgY immunoglobulin constant domains were synthesised from cDNA derived from chicken splenocytes. The 5' end of the chicken υ1 heavy chain was amplified using the PCR primer (accgaagtcatcgtctcctc, SEQ ID NO:3) and (cctcagtttggcgtctaagc, SEQ ID NO:4). The 3' end was amplified using the PCR primer (gaggatcacgtcaagggatg, SEQ ID NO:5) and (gcacccccaatcctttattt, SEQ ID NO:6). After hybridization of these two fragments the complete chicken υ1 heavy chain was amplified using the PCR primer (accgaagtcatcgtctcctc, SEQ ID NO:7) and (gcacccccaatcctttattt, SEQ ID NO:8). Amplification by PCR was performed as described in example 1.

2.1. Amplification υ1 $C_H$1-4 domains. The chicken υ1 $C_H$1-4 domains were amplified using one PCR primer containing an Asc I site (gatcggcgcgcccgcgagccccacatcgcc, SEQ ID NO:9) and another PCR primer containing a Xba I site and a 4×His overhang (gatctctagatcagtgatggtgatgtttaccagcctgtttctg, SEQ ID NO:10).

2.2. Amplification υ1 $C_H$2-4 domains. The υ1 $C_H$2-4 domains were amplified using one PCR Primer containing an Asc I site (gatcggcgcgccgcctgtagccccagag, SEQ ID NO:11) and another Primer containing a Xba I site and a 4×His overhang (gatctctagatc agtgatggtgatgtttaccagcctgtttctg, SEQ ID NO:12).

2.3. Amplification υ1 $C_H$3-4 domains. The υ1 $C_H$3-4 domains were amplified using one PCR primer containing an Asc I site (gatcggcgcgcccggcgctcagagctgc, SEQ ID NO:13) and another PCR primer containing a Xba I site and a 4×His overhang (gatctctagatcagtgatggtgatgtttaccagcctgtttctg, SEQ ID NO:14).

2.4. Amplification υ1 $C_H$1-2 domains. The υ1 $C_H$1-2 domains were amplified using one PCR primer containing an Asc I site (gatcggcgcgcccgcgagccccacatcgcc, SEQ ID NO:15) and another PCR primer containing a Xba I site and a 4×His overhang (gatctctagatcagtgatggtgatggaactccgggcatcccttgacgtgatc, SEQ ID NO:16).

2.5. Amplification υ1 $C_H$2 domain. The υ1 $C_H$2 domain was amplified using one PCR primer containing an Asc I site (gatcggcgcgccgcctgtagccccagag, SEQ ID NO:17) and another PCR primer containing a Xba I site and a 4×His overhang (gatctctagatcagtgatggtgatggaactccgggcatcccttgacgtgatc, SEQ ID NO:18).

Example 3

Amplification of the Rodent κ Light Chain Leader Sequence

The signal sequence of a rodent κ light chain was assembled by 2 PCR primers containing a Nhe I site (gtacaagcttgctagcaagatggaatcacagacccaggtcctcatgtccctgctgctc, SEQ ID NO:19) and another primer (atgtccctgctgctcgatttctggtacctgtggggtccctcagaaacctaag, SEQ ID NO:20). Amplification by PCR was performed as described in example 1.

Example 4

Cloning of Constructs Comprising FcεRIα-ecd And IgY Constant Domains

For convenient expression of the constructs of the invention a set of modular cassettes containing IgY constant immunoglobulin domains, and restriction sites for the incorporation of FcεRIα-ecd was generated.

The individual IgY constant immunoglobulin domains immunoglobulin were inserted via Asc I and Xba I into the mammalian expression vector pcDNA3.1-zeo (Invitrogen life technologies, Karlsruhe, Germany) containing the rodent K light chain leader sequence. Introduction of FcεRIα-ecd into the vector was performed by introduction of a BsiW I site at the N-terminus (gatccgtacgtgtggggccgtgacgttggacg, SEQ ID NO:21) and an Asc I site at the C-terminus (gatcggcgcgccacctaggacggtcaggg, SEQ ID NO:22) of the receptor fragment by PCR. Subsequently, the DNA was ligated into the vector pcDNA3.1-zeo (Invitrogen life technologies, Karlsruhe, Germany) containing the signal sequence and the particular constant regions.

Example 5

Cloning of Constructs Comprising FcεRIα-ecd and Mono- or Non-Glycosylated IgY Constant Domains The site-directed mutagenesis was performed using the QuikChange site-directed mutagenesis kit (Stratagene, La Jolla, USA). For substitution of the glycosylation site in position 407 the expression vector pcDNA3.1-zeo (Invitrogen life technologies, Karlsruhe, Germany) modified as described in example 4 was amplified using the PCR primer (ggtcctccaagaacactt ccagggcacctacagcgccagc, SEQ ID NO:23) and the PCR primer (gctggcgctgtaggtgccctggaagtgtccttggaggacc, SEQ ID NO:24). For substitution of the glycosylation site in position 308 the expression vector pcDNA3.1-zeo (Invitrogen life technologies, Karlsruhe, Germany) modified as described in example 4 was amplified using the PCR primer (gcctgagcagccgcgtcca ggtcagcggcaccgattgg, SEQ ID NO:25) and the PCR primer (ccaatcggtgccgctgacctggacgcggctgctcaggc, SEQ ID NO:26). Correctness of the mutations was verified by DNA sequencing.

Example 6

Cloning of FcεRIα-Constructs and Prokaryotic Expression

For prokaryotic expression the human FcεRIα extracellular domain was amplified using one PCR primer containing an Nde I site (gatccatatggcagtccctcagaaacctaag, SEQ ID NO:27) and another primer containing a Not I site (gatcgcggccgccggagcttttattacagtaatgttgag, SEQ ID NO:28), and introduced into the procayotic expression vector pET26b+ (Novagen, Schwalbach, Germany).

The plasmids encoding the FcεRIα-ecd was transformed in the *E. coli* K12 strain BL21 Ril DE3. Small-scale expressions were performed at 30° C. using 100 ml 2YT medium (16 g/liter tryptone, 10 g/liter yeast extract, 5 g/liter NaCl) containing 50 µg/ml kanamycin. Cultures were inoculated from a 10 ml preculture to $OD_{550}$=0.1. Expression was induced with 1 mM IPTG at an $OD_{550}$ between 1.0 and 1.5. Cells were harvested 3 h after induction by centrifugation and resuspended in PBS buffer (20 mM $NaH_2PO_4$, 500 mM NaCl, 0.1 mM EDTA, pH 7.2) using 1 ml buffer per mg cells. Whole cell extracts were prepared by sonification and crude extract was centrifuged in an Eppendorf tube for 60 min at 20.000×g and 4° C. The supernatants containing the soluble material were passed through a 22 μm filter (Millipore, Germany).

Example 7

Eukaryotic Expression of Constructs Comprising FcεRIα-ecd and IgY Constant Domains HEK-293 cells (ATCC number CRL-1573) were cultivated in DMEM (Dulbecco's modified Eagle Medium) supplemented with 10% (v/v) heat-inactivated fetal calf serum, 100 IU/ml penicillin, and 100 μg/ml streptomycin. Tissue culture reagents were obtained from Invitrogen life technologies (Karlsruhe, Germany). HEK-293 cells growing in DMEM supplemented with 10% (v/v) fetal calf serum were transfected with 2 μg of the particular expression vector using PEI (polyethylenimine, Sigma, Taufkirchen, Germany). Stable transfectants then were selected in DMEM supplemented with 10% (v/v) fetal calf serum and 100 μg/ml of zeocin (Invitrogen life technologies, Karlsruhe, Germany).

For expression of the constructs, transfected cells were grown for 3 days as an adhesion culture. The constructs secreted by transfected HEK-293 cells were purified from the culture medium by affinity chromatography using Ni-NTA-agarose (Qiagen, Hilden, Germany) according to the manufacturers recommendations.

As an example, FIG. 6 shows the analysis by SDS-PAGE (A) and immunoblot (B) of a homodimeric FcεRIα construct (FcεRIα-IgY$_{CH1-4}$His, construct I) comprising IgY constant domains $C_H1$-$C_H4$, expressed and purified as described. For immunoblot analysis, purified recombinant FcεRIα —IgY$_{CH1-4}$His was separated by SDS-PAGE using a tris/glycin-buffered 10% polyacrylmide gel. The proteins were transferred onto a nitrocellulose membrane by western blotting. After incubation for 90 min at room temperature on a rocker platform, the blot membrane was rinsed 3 times with Tween (0.1% v/v)-phosphate-buffered saline (TPBS) and PBS and further incubated with 10 ml of anti-chicken-IgG-AP conjugate (diluted in phosphate-buffered saline-milk powder (2% w/v), Sigma, Taufenstein, Germany) for 60 min at room temperature on a rocker platform. The membrane was rinsed again 3 times each with 0.1% (v/v) TPBS and PBS and FcεRIα-IgY$_{CH1-4}$His was visualized by the addition of 10 ml of a BCIP/NBT substrate solution diluted in 100 mM Tris-HCl, pH 9.5 (Sigma, Taufenstein, Germany) until bands became visible.

Example 8

Immunoreactivity of Constructs Comprising

FcεRIαecd and IgY Constant Domains
Purified recombinant human IgE was diluted in phosphate-buffered saline-2% (w/v) milk powder (MPBS; Sigma, Taufen-stein, Germany) containing 10% (w/v) fetal calf serum (FKS, Biochrom, Germany), applied to microtiter plates at 4° C. overnight, and blocked with 10% (w/v) FKS at room temperature for 2 h. After incubation of the microtiter plates for 90 min at room temperature on a rocker platform, the wells were rinsed 3 times each with Tween (0.1% v/v)-phosphate-buffered saline (TPBS) and PBS and further incubated with 100 μl each of cell culture supernatant FcεRIα-IgY$_{CH1-4}$His (construct I) (diluted in 10% (w/v) FKS) for 60 min at room temperature on a rocker platform. The wells were rinsed again 3 times each with 0.1% (v/v) TPBS and PBS and further incubated with 100 μl each of polyclonal anti-chicken-IgG-AP conjugate (diluted 1:1000 in 10% FKS, Sigma, Taufenstein, Germany) for 60 min at room temperature on a rocker platform. The wells were rinsed again 3 times each with 0.1% (v/v) TPBS and PBS and bound antibodies were visualized by the addition of 75 μl of a 4-nitrophenyl disodium orthophosphate substrate solution (Sigma, Taufenstein, Germany). Absorbance was determined at 405 nm after 20 min of incubation. Data of the experiment are shown in FIG. 6C.

Example 9

Figure 7:
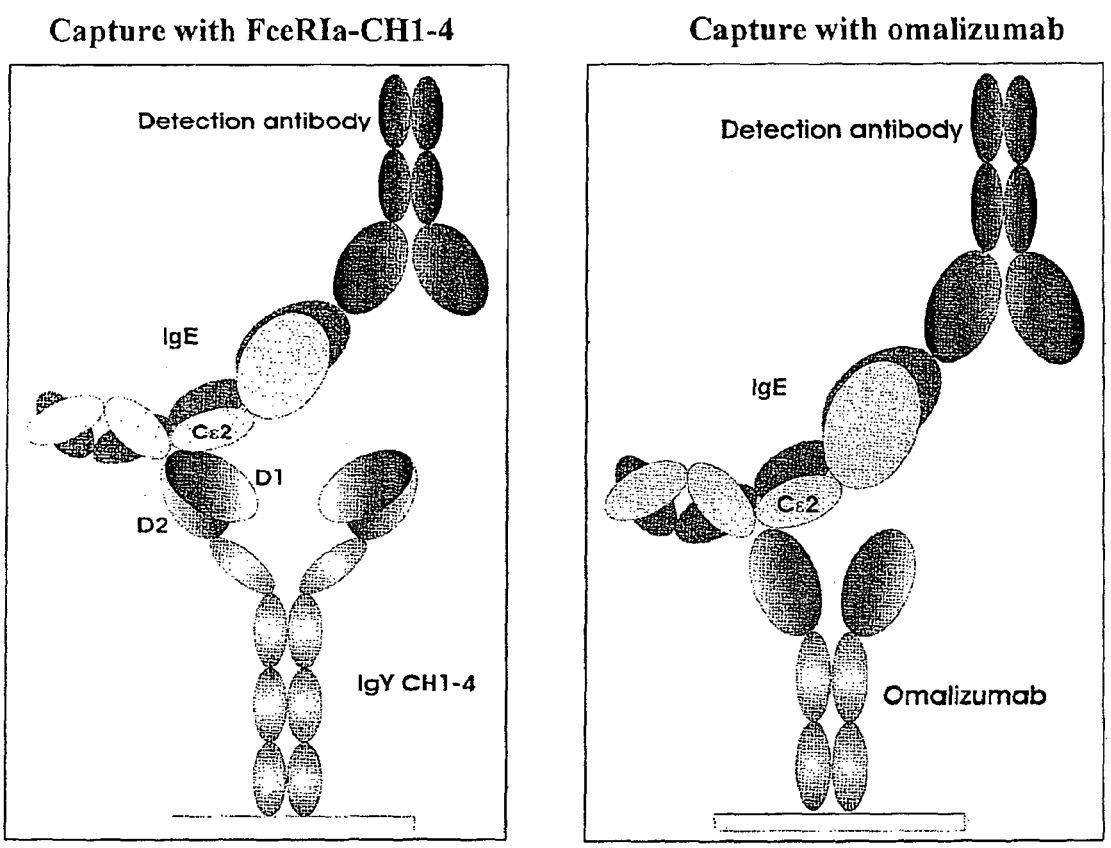
Figure 9:
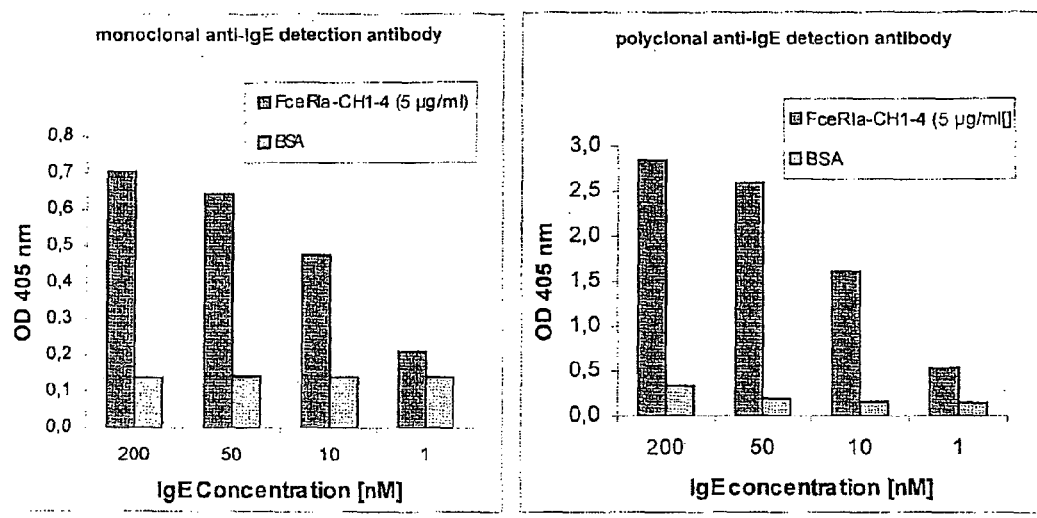

Quantitation of Recombinant Human IgE Using FcεRIα-IgY$_{CH1-4}$His as Capture Reagent The assay principle is illustrated in FIG. 7 (left panel). Human IgE is captured by immobilized FcεRIα-IgY$_{CH1-4}$His (construct I) and captured IgE is detected with monoclonal anti-human IgE (clone GE-1, Sigma, Taufenstein, Germany) and anti-mouse IgG-AP conjugate (FIG. 9, left panel) or with polyclonal anti-human IgE-AP conjugate (FIG. 9, right panel).

Purified FcεRIα-IgY$_{CH1-4}$His (construct I) (diluted with phosphate buffered saline-milk powder (2% (w/v), MPBS) was applied to microtiter plates at 4° C. overnight and blocked with MPBS at room temperature for 2 h. After incubation of the microtiter plates for 90 min at room temperature on a rocker platform, the wells were rinsed 3 times each with) Tween (0.1% v/v)-PBS (TPBS) and PBS and further incubated with 100 μl each of recombinant human IgE (diluted 100 nM to 0.1 nM in 2% (w/v) MPBS) for 60 min at room temperature on a rocker platform. The wells were rinsed again 3 times each with 0.1% (v/v) TPBS and PBS and further incubated with 100 μl each of polyclonal anti-human IgE-HRP conjugate (diluted 1:1000 in 2% (w/v) MPBS, Sigma, Taufenstein, Germany) for 60 min at room temperature on a rocker platform. The wells were rinsed again 3 times each with 0.1% (v/v) TPBS and PBS and bound antibodies were visualized by the addition of 75 μl of a 4-nitrophenyl disodium orthophosphate substrate solution (Sigma, Taufenstein, Germany). Absorbance was determined at 405 nm after 20 min of incubation. Data of the experiment are shown in FIG. 9.

Example 10

Quantitation of Human Myeloma IgE Using FcεRIα —IgY$_{CH1-4}$His AS Capture Reagent The assay principle is illustrated in FIG. 7 (left panel). Human IgE is captured by immobilized FcεRIα-IgY$_{CH1-4}$His (construct I) and captured IgE is detected with a biotinylated murine anti-human IgE antibody and an avidin-horseradish peroxidase complex.

To prepare IgE standards, a human serum containing a very low total IgE concentration (<1 U/ml) was spiked with pre-defined amounts of purified human myeloma IgE (range: 0-4,000 μg/ml). As an alternative, the same standard range of IgE was prepared in assay diluent buffer, which is part of a set of ready-to-use ELISA reagents (Pharmingen, 550534).

ELISA plates (Greiner) were coated overnight at 4° C. with 100 μl/well of FcεRIα-IgY$_{CH1-4}$His (construct I) containing coating buffer solution (part of Pharmingen kit 550534) at coating concentrations of 1 or 10 μg/ml. The coating solution was removed and the plates were washed three times with 300 μl washing buffer (part of Pharmingen kit). Subsequently, unoccupied sites were blocked by incubating for 1 h at room temperature with 200 μl/well of assay diluent buffer. After washing three times with 300 μl/well of washing buffer, IgE standard range solutions and controls (diluted 1:10 in assay diluent buffer) were added to the appropriate wells (100 μl/well) in duplicate and incubated for 2 h at room temperature. The plates were washed again five times with 300 μl/well of washing buffer. Subsequently, 100 μl of a detector mix solution were added per well, containing a biotinylated murine anti-human IgE antibody (BD, 555858) and an avidin-horseradish peroxidase (HRP) complex (BD), both diluted 1:250 in assay diluent buffer, and incubated for 1 h at room temperature. Plates were washed seven times (300 μl/well), followed by the addition of 100 μl/well of substrate solution (part of the Pharmingen kit) and incubation for 30 min at room temperature in the dark. The substrate reaction was terminated by the addition of 50 μl/well of stop solution (Pharmingen kit). The optical density was read at 450 nm using a Dynex MRX II ELISA reader. The working range of the assay was between 31 and 4,000 μg/ml. Data of the experiment are shown in FIG. 10 (upper panel).

Example 11

Quantitation of Human Myeloma IgE Using Omalizumab (Xolair®) AS Capture Antibody The assay principle is illustrated in FIG. 7 (right panel). Human IgE is captured by immobilized omalizumab (Xolair®) and captured IgE is detected with a biotinylated murine anti-human IgE antibody and an avidin-horseradish peroxidase complex.

Human myeloma IgE standard solutions (range: 0-4,000 μg/ml) were prepared asw described in example 10. ELISA plates (Greiner) were coated overnight at 4° C. with 100 μl/well of omalizumab (Xolair®) containing coating buffer solution (part of Pharmingen kit 550534) at coating concentrations of 1 or 10 μg/ml. The coating solution was removed and the plates were washed three times with 300 μl washing buffer (part of Pharmingen kit). Subsequently, unoccupied sites were blocked by incubating for 1 h at room temperature with 200 μl/well of assay diluent buffer. After washing three times with 300 μl/well of washing buffer, IgE standard range solutions and controls (diluted 1:10 in assay diluent buffer) were added to the appropriate wells (100 μl/well) in duplicate and incubated for 2 h at room temperature. The plates were washed again five times with 300 μl/well of washing buffer. Subsequently, 100 μl of a detector mix solution were added per well, containing a biotinylated murine anti-human IgE antibody (BD, 555858) and an avidin-horseradish peroxidase (HRP) complex (BD), both diluted 1:250 in assay diluent buffer, and incubated for 1 h at room temperature. Plates were washed seven times (300 μl/well), followed by the addition of 100 μl/well of substrate solution (part of the Pharmingen kit) and incubation for 30 min at room temperature in the dark. The substrate reaction was terminated by the addition of 50 μl/well of stop solution (Pharmingen kit). The optical density was read at 450 nm using a Dynex MRX II ELISA reader. The working range of the assay was between 31 and 4,000 μg/ml. Data of the experiment are shown in FIG. 10 (lower panel).

Example 12

Figure 8:
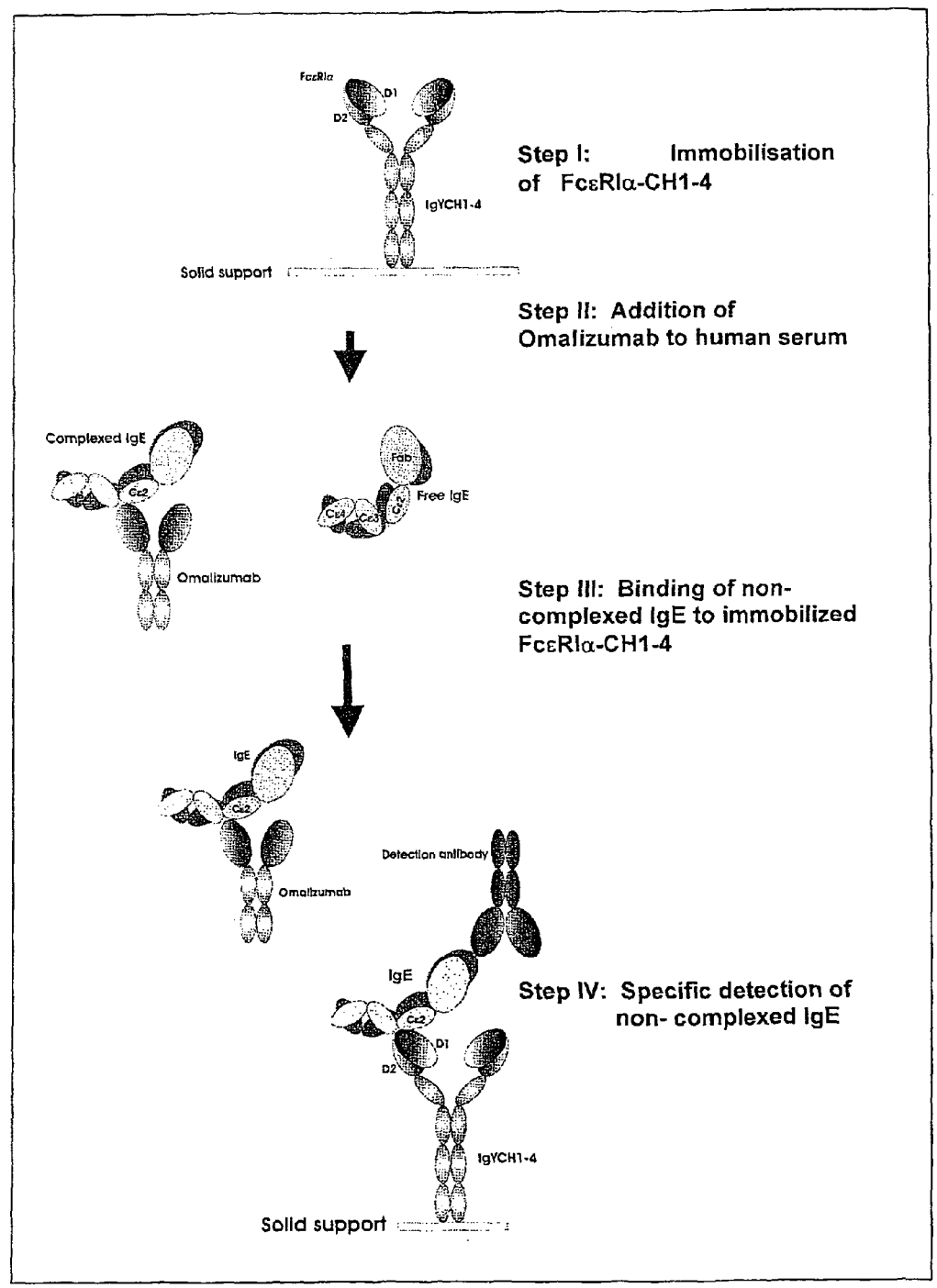

Quantitation of Human IgE in the Presence of IgE/Anti-IgE-Complexes Using FcεRIα-IgY$_{CH1-4}$His as Capture Reagent The assay principle is illustrated in FIG. 8. Human IgE that is not complexed with omalizumab is captured by immobilized FcεRIα-IgY$_{CH1-4}$His (construct I) and captured IgE is detected with a biotinylated murine anti-human IgE antibody and an avidin-horseradish peroxidase complex.

For the preparation of complexed IgE, human myeloma IgE was added to IgE-negative normal human serum (total serum IgE concentration <1 U/ml) at a final concentration of 10 ng/ml.

Anti-IgE antibody omalizumab (Xolair®) was added to these IgE-containing sera at a final concentration of 0.002 to 200 μg/ml. Thus, concentration-dependent amounts of IgE-containing complexes and free IgE were generated.

Free IgE was measured using an ELISA technique with FcεRIα-IgY$_{CH1-4}$His (construct I) as capture reagent. This avoids detection of IgE that is already complexed with omalizumab and thus measures both baseline IgE levels before anti-IgE treatment and remaining free (uncomplexed) IgE after anti-IgE treatment.

A biotinylated monoclonal murine anti-IgE which was specific for an epitope of the human IgE molecule different from that of omalizumab and FcεRIα was used as the secondary (revealing) antibody.

ELISA plates (Greiner) were coated overnight at 4° C. with 100 μl/well of FcεRIα-IgY$_{CH1-4}$His (construct I) containing coating buffer solution (part of Pharmingen kit 550534) at coating concentrations of 1 or 10 μg/ml. The coating solution was removed and the plates were washed three times with 300 μl washing buffer (part of Pharmingen kit). Subsequently, unoccupied sites were blocked by incubating for 1 h at room temperature with 200 μl/well of assay diluent buffer. After washing three times with 300 μl/well of washing buffer, sera containing free IgE and IgE/anti-IgE-complexes and controls (diluted 1:10 in assay diluent buffer) were added to the appropriate wells (100 μl/well) in duplicate and incubated for 2 h at room temperature. The plates were washed again five times with 300 μl/well of washing buffer. Subsequently, 100 μl of a detector mix solution were added per well, containing the biotinylated murine anti-human IgE antibody (BD, 555858) and an avidin-horseradish peroxidase (HRP) complex (BD), both diluted 1:250 in assay diluent buffer, and incubated for 1 h at room temperature. Plates were washed seven times (300 μl/well), followed by the addition of 100 μl/well of substrate solution (part of the Pharmingen kit) and incubation for 30 min at room temperature in the dark. The substrate reaction was terminated by the addition of 50 μl/well of stop solution (Pharmingen kit). The optical density was read at 450 nm using a Dynex MRX II ELISA reader. The working range of the assay was between 31 and 4,000 μg/ml.

Example 13

Quantitation of Human IgE in the Presence of IgE/FcεRIαα-IgY$_{CH1-4}$His-Complexes Using Omalizumab (Xolair®) as Capture Antibody The assay principle is illustrated in FIG. 8. Immobilized omalizumab ist utilized as capture antibody instead of FcεRIα-IgY$_{CH1-4}$His (construct I). Human IgE that is not complexed with FcεRIα-IgY$_{CH1-4}$His (construct I) is captured by immobilized omalizumab and captured IgE is detected with a biotinylated murine anti-human IgE antibody and an avidin-horseradish peroxidase complex.

For the preparation of complexed IgE, human myeloma IgE was added to IgE-negative normal human serum (total serum IgE concentration <1 U/ml) at a final concentration of 10 ng/ml. FcεRIα-IgY$_{CH1-4}$His (construct I) was added to these IgE-containing sera at a final concentration of 0.002 to 200 μg/ml. Thus, concentration-dependent amounts of IgE-containing complexes and free IgE were generated.

Free IgE was measured using an ELISA technique with omalizumab (Xolair®) as capture antibody. A biotinylated monoclonal murine anti-IgE which was specific for an epitope of the human IgE molecule different from that of omalizumab and FcεRIα was used as the secondary (revealing) antibody.

Figure 11:
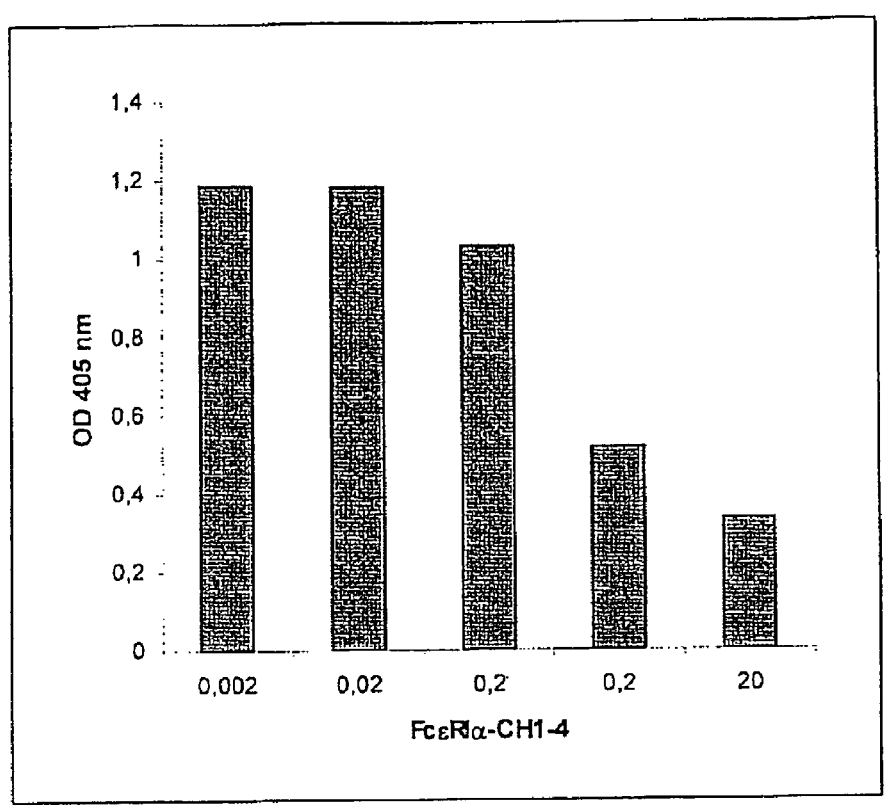

ELISA plates (Greiner) were coated overnight at 4° C. with 100 μl/well of omalizumab (Xolair®) containing coating buffer solution (part of Pharmingen kit 550534) at coating concentrations of 1 or 10 μg/ml. The coating solution was removed and the plates were washed three times with 300 μl washing buffer (part of Pharmingen kit). Subsequently, unoccupied sites were blocked by incubating for 1 h at room temperature with 200 μl/well of assay diluent buffer. After washing three times with 300 μl/well of washing buffer, sera containing free IgE and IgE/anti-IgE-complexes and controls (diluted 1:10 in assay diluent buffer) were added to the appropriate wells (100 µl/well) in duplicate and incubated for 2 h at room temperature. The plates were washed again five times with 300 µl/well of washing buffer. Subsequently, 100 µl of a detector mix solution were added per well, containing the biotinylated murine anti-human IgE antibody (BD, 555858) and an avidin-horseradish peroxidase (HRP) complex (BD), both diluted 1:250 in assay diluent buffer, and incubated for 1 h at room temperature. Plates were washed seven times (300 µl/well), followed by the addition of 100 µl/well of substrate solution (part of the Pharmingen kit) and incubation for 30 min at room temperature in the dark. The substrate reaction was terminated by the addition of 50 µl/well of stop solution (Pharmingen kit). The optical density was read at 450 nm using a Dynex MRX II ELISA reader. The working range of the assay was between 31 and 4,000 µg/ml. Data of the experiment are shown in FIG. 11.

Example 14

Quantitation of Human IgE in the Presence of IgE/Anti-IgE-Complexes Using Omalizumab (Xolair®) as Capture Antibody The assay principle is illustrated in FIG. 8. Immobilized omalizumab ist utilized as capture antibody instead of FcεRIα-IgY$_{CH1-4}$His (construct I). Human IgE that is not complexed with omalizumab is captured by immobilized omalizumab and captured IgE is detected with a biotinylated murine anti-human IgE antibody and an avidin-horseradish peroxidase complex.

For the preparation of complexed IgE, human myeloma IgE was added to IgE-negative normal human serum (total serum IgE concentration <1 U/ml) at a final concentration of 10 ng/ml. Anti-IgE antibody omalizumab (Xolair®) was added to these IgE-containing sera at a final concentration of 0.002 to 200 µg/ml. Thus, concentration-dependent amounts of IgE-containing complexes and free IgE were generated.

Free IgE was measured using an ELISA technique with omalizumab (Xolair®) as capture antibody. A biotinylated monoclonal murine anti-IgE which was specific for an epitope of the human IgE molecule different from that of omalizumab and FcεRIα was used as the secondary (revealing) antibody.

Figure 12:
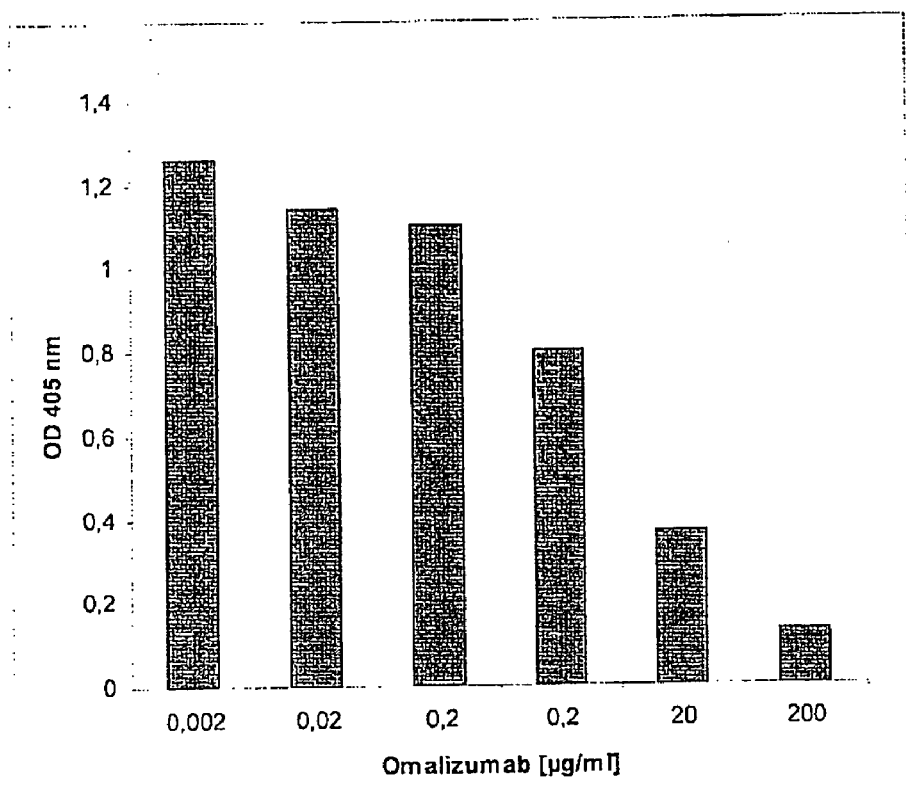
Figure 13:
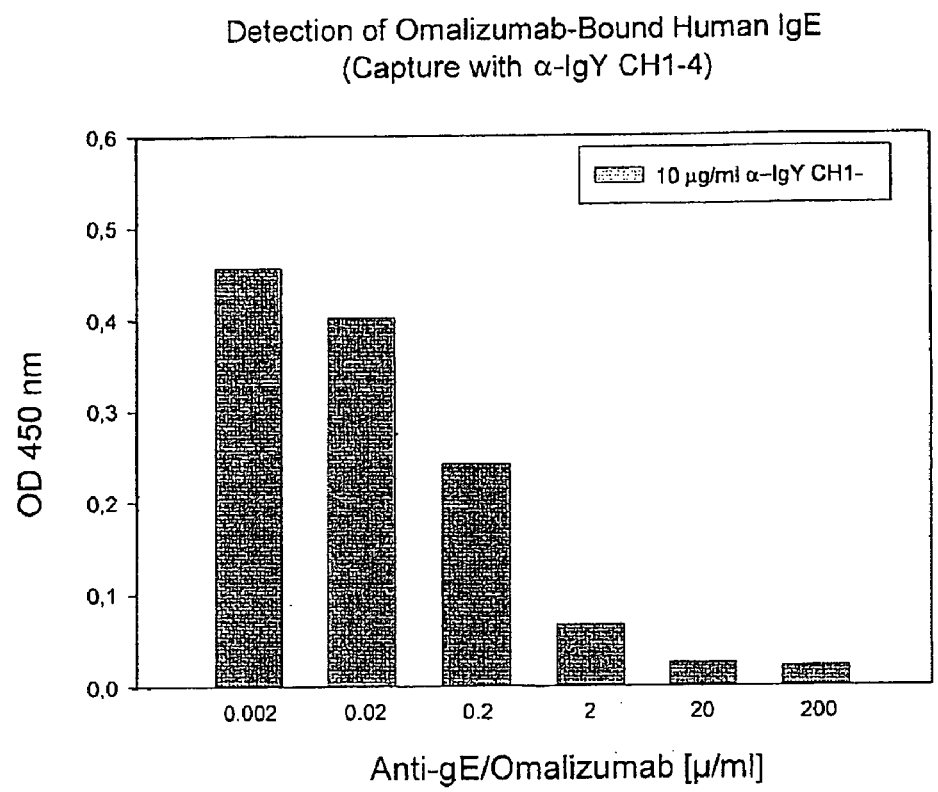
Figure 13:
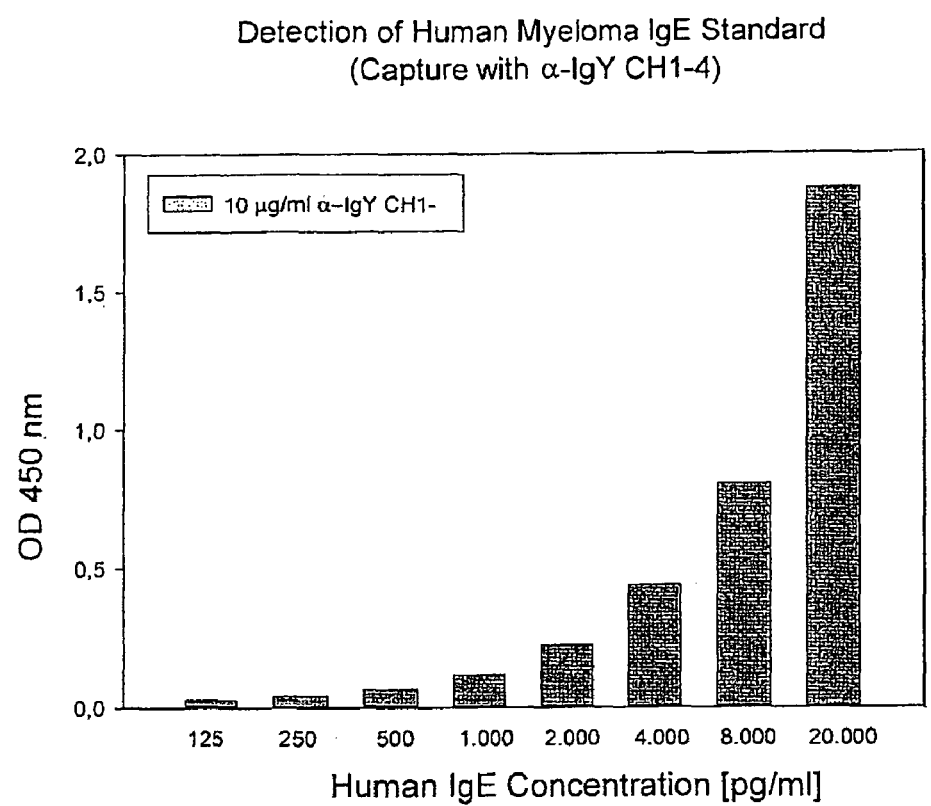

ELISA plates (Greiner) were coated overnight at 4° C. with 100 µl/well of omalizumab (Xolair®) containing coating buffer solution (part of Pharmingen kit 550534) at coating concentrations of 1 or 10 µg/ml. The coating solution was removed and the plates were washed three times with 300 µl washing buffer (part of Pharmingen kit). Subsequently, unoccupied sites were blocked by incubating for 1 h at room temperature with 200 µl/well of assay diluent buffer. After washing three times with 300 µl/well of washing buffer, sera containing free IgE and IgE/anti-IgE-complexes and controls (diluted 1:10 in assay diluent buffer) were added to the appropriate wells (100 µl/well) in duplicate and incubated for 2 h at room temperature. The plates were washed again five times with 300 µl/well of washing buffer. Subsequently, 100 µl of a detector mix solution were added per well, containing the biotinylated murine anti-human IgE antibody (BD, 555858) and an avidin-horseradish peroxidase (HRP) complex (BD), both diluted 1:250 in assay diluent buffer, and incubated for 1 h at room temperature. Plates were washed seven times (300 µl/well), followed by the addition of 100 µl/well of substrate solution (part of the Pharmingen kit) and incubation for 30 min at room temperature in the dark. The substrate reaction was terminated by the addition of 50 µl/well of stop solution (Pharmingen kit). The optical density was read at 450 nm using a Dynex MRX II ELISA reader. The working range of the assay was between 31 and 4,000 µg/ml. Data of the experiment are shown in FIG. 12.

REFERENCES

Basu M, Hakimi J, Dharm E, Kondas A J, Tsien W H, Pilson R S, Lin P, Gilfillan A, Haring P, Braswell E H, et al. Purification and characterization of human recombinant IgE-Fc fragments that bind to the human high affinity IgE receptor. J. Biol. Chem. 268, 13118-13127, 1993.

Beasley R, Crane J, Lai C K, Pearce N. Prevalence and etiology of asthma. J Allergy Clin Immunol 105: 466-472, 2000.

Blank U, Ra C, Kinet J-P. Characterization of truncated a chain products from human, rat, and mouse high affinity receptor for immunoglobulin E. J Biol Chem 266, 2639-2646, 1991.

Boscato L, Stuart M. Incidence and Specificity of interference in Two-site immunoassays. Clin chem 32, 1491-1495, 1986.

Boscato L M, Stuart M C. Heterophilic antibodies: a problem for all immunoassays. Clin Chem 34, 27-33, 1988.

Burrows B, Martinez F D, Halonen M, Barbee R A, Cline MG. Association of asthma with serum IgE levels and skin-test reactivity to allergens. N Engl J Med 320: 271-277, 1989.

Campbell R D, Dodds A W, Porter R R. The binding of human complement component C4 to antibody-antigen aggregates. Biochem J 189, 6780, 1980.

Conrad DH. Fc epsilon RII/CD23: the low affinity receptor for IgE. Ann Rev Immunol 8: 623-645, 1990.

Doyle R. Asthma worldwide. Sci Am 282: 30, 2000.

Figdor C G, van Kooyk Y, Adema G J. C-Type lectin receptors on dendritic cells and Langerhans cells. Nature Rev. Immunol. 2, 77-84, 2002.

Garman S C, Kinet J-P, Jardetzky T S. The crystal structure of the human high-affinity IgE receptor (FcεRIα). Annu Rev Immunol 17: 973-976, 1999.

Haak-Frendscho M, Ridgway J, Shields R, Robbins K, Gorman C, Jardieu P. Human IgE receptor α-chain IgG chimera blocks passive cutaneous anaphylaxis reaction in vivo. J Immunol 151: 351-358, 1993.

Hamelmann E, Rolinck-Werninghaus C, Wahn U. From IgE to anti-IgE: where do we stand? Allergy 57: 983-994, 2002.

Hamelmann E, Rolinck-Werninghaus C, Wahn U. Is there a role for anti-IgE in combination with specific allergen immunotherapy? Curr Opin Allergy Clin Immunol 3: 501-510, 2003.

Hara T, Yamada K, Tachibana H. Basophilic differentiation of the human leukemia cell' line KU812 upon treatment with interleukin-4. Biochem Biophys Res Commun 247: 542, 1998.

Johnson P M, Faulk W P. Rheumatoid factor: its nature, specificity, and production in rheumatoid arthritis. Clin Immunol Immunopathol 6, 414-430, 1976.

Kapyaho K, Tanner P, Weber T. Effect of complement binding on a solid phase immunometric TSH assay. Scand J Clin Lab Invest 49, 211215, 1989.

Kinet J-P. The high-affinity IgE receptor (FcεRI): from physiology to pathology, Annu Rev Immunol 17: 931-972, 1999.

Kricka L J. Human anti-animal antibody interferences in immunological assays. Clin Chem 45, 942-956, 1999.

Larsson A, Sjoquist J. Binding of complement components Clq, C3, C4 and C5 to a model immune complex in ELISA. J Immunol Methods 119, 103-109, 1989.

Larsson A, Karlsson-Parra A, Sjoquist J. Use of chicken antibodies in enzyme immunoassays to avoid interference by rheumatoid factors. Clin Chem 37, 411-414, 1991.

Larsson A, Mellstedt H. Chicken antibodies: a tool to avoid interference by human anti-mouse antibodies in ELISA after in vivo treatment with murine monoclonal antibodies. Hybridoma 11, 33-39, 1992.

Larsson A, Wejaker P E, Forsberg P O, Lindahl T. Chicken antibodies: a tool to avoid interference by complement activation in ELISA. J Immunol Methods 156, 79-83, 1992.

Leslie G A, Clem L W. Phylogen of immunoglobulin structure and function. Immunoglobulins of the chicken. J Exp Med 130, 1337-1352, 1969.

Letourner O, Sechi S, Wilette-Brown J, Robertson M W, Kinet JP. Glycosylation of human truncated FcεRIα-chain is necessary for efficient folding in the endoplasmic reticulum. J Biol Chem 270: 8249-8256, 1995.

Lowe J, Jardieu P, VanGorp K, Fei D T. Allergen-induced histamine release in rat mast cells transfected with the alpha subunits of Fc epsilon RI. J Immunol Meth 184: 113, 1995.

Malhotra R., Wormald M R, Rudd P M, Fischer P B, Dwek R A, Sim R B. Glycosylation changes of IgG associated with rheumatoid arthritis can activate complement via the mannose-binding protein. Nat. Med. 1, 237-243, 1995.

Ostergaard P A, Ebbesen F, Nolte H, Skov P S. Basophil histamine release in the diagnosis of house dust mite and dander allergy of asthmatic children. Comparison between prick test, RAST, basophil histamine release and bronchial provocation. Allergy 45: 231, 1990.

Presta L G, Lahr S J, Shields R L, et al. Humanization of an antibody directed against IgE. J Immunol 151: 2623-2632, 1993.

Pruzansky J J, Grammer L C, Patterson R, Roberts M. Dissociation of IgE from receptors on human basophils. I. Enhanced passive sensitization for histamine release. J Immunol 131: 1949, 1983.

Ravetch J V, Kinet J-P. Fc receptors. Annu Rev Immunol 9: 457, 1991.

Reid, M. J., Moss, R. B., Hsu, Y. P., Kwasnicki, J. M., Commerford, T. M., Nelson, B. L. Seasonal asthma in northern California: allergic causes and efficacy of immunotherapy. J. Allergy Clin. Immunol. 78, 590-600, 1986.

Robertson M W. Phage and *Escherichia coli* expression of the human high affinity immunoglobulin E receptor alpha-subunit ectodomain. Domain localization of the IgE-binding site. J Biol Chem 268: 12736-12743, 1993.

Roos A, Bouwman L H, van Gijlswijk-Janssen D J, Faber-Krol M C, Fallaux-van den Houten F C, Klar-Mohamad N, Hack C E, Tilanus M G, Daha M R. Human IgA activates the complement system via the mannan-binding lectin pathway. J. Immunol. 167, 2861-

Saban R, Haak-Frendscho M, Zine M, et al. Human FcεRI-IgG and humanized anti-IgE monoclonal antibody MaE11 block passive sensitization of human and rhesus monkey lung. J Allergy Clin Immunol 94: 836-843, 1994.

Sambrook J, Fritsch E F, Maniatis T. Molecular Cloning. A Laboratory Manual, second ed., Cold Spring Harbor Press, 1989.

Scarselli E, Esposito G, Traboni C. Receptor phage. Display of functional domains of the human high affinity IgE receptor on the M13 phage surface. FEBS Lett 329: 223-226, 1993.

Sun S, Mo W, Il Y, Liu S. Preparation and mass spectrometric study of egg yolk antibody (IgY) against rabies virus. Rapid Commun Mass Spectrom 15, 708-712, 2001.

Suzuki N, Khoo K H, Chen C M, Chen C H, Lee Y C. N-glycan structures of pigeon IgG: a major serum glycoprotein containing Galα1-4Gal termini J. Biol. Chem. 278, 46293-46306, 2003.

Suzuki N, Lee Y C. Site-specific N-glycosylation of chicken serum IgG. Glycobiology 14, 275-292, 2004.

Takahashi N, Nakagawa H, Fujikawa K, Kawamura Y, Tomiya N. Three-dimensional elution mapping of pyridylaminated N-linked neutral and sialyl oligosaccharides. Anal. Biochem. 226, 139-146, 1995.

Van de Wetering J K., van Golde L M G, Batenburg J J. Collectins. Players of thevinnate immune system. Eur. J. Biochem. 271, 1229-1249, 2004.

Varney, V. A., Hamid, Q. A., Gaga, M., et al. Influence of grass pollen immunotherapy on cellular infiltration and cytokine mRNA expression during allergen-induced late-phase cutaneous responses. J. Clin. Invest. 92, 644-651, 1993.

Verma R, Boleti E, George A J T. Antibody engineering: Comparison of bacterial, yeast, insect and mammalian expression systems. J Immunol Meth 216: 165-181, 1998.

Wan T, Beavil R L, Fabiane S M, Beavil A J, Sohi M K, Keown M, Young R J, Henry A J, Owens R J, Gould H J, Sutton B J. The crystal structure of IgE Fc reveals an asymmetrically bent conformation. Nat. Immunol. 3, 681-686, 2002.

Warr G W, Magor K E, Higgins D A. IgY: clues to the origins of modern antibodies. Immunol Today 16, 392-398, 1995.

---

What is claimed is:

1. A chimeric fusion construct comprising the extracellular portion of human FcεRIα and an IgY constant immunoglobulin domain selected from the group consisting of a CH2 constant domain; a CH3 constant domain; a CH4 constant domain; a CH1 and a CH3 constant domain; a CH1 and a CH4 constant domain; a CH2 and a CH3 constant domain; a CH2 and a CH4 constant domain; a CH3 and a CH4 constant domain; a CH1, a CH2, and a CH4 constant domain; a CH1, a CH3, and a CH4 constant domain; a CH2, a CH3, and a CH4 constant domain; and a CH1, a CH2, and a CH3 constant domain; and wherein the construct is homodimeric.

2. The fusion construct of claim 1, wherein the extracellular portion of human FcεRIα has the amino acid sequence as shown in SEQ ID NO:32.

3. The fusion construct of claim 1, wherein one or more glycosylation site(s) of the immunoglobulin domain(s) is(are) mutated by site-directed mutatgenesis.

4. The fusion construct of claim 3, wherein the IgY constant domain(s) is(are) monoglycosylated.

5. The fusion construct of claim 3, wherein the IgY constant domain(s) is(are) non-glycosylated.

6. The fusion construct of claim 1, wherein the amino acids E and F are fused to the carboxy-terminal end of the IgY $C_H2$-domain.

7. The fusion construct of claim 1, wherein one or more glycosylation site(s) of the extracellular portion of human FcεRIα is(are) mutated by site-directed mutatgenesis.

8. A nucleic acid molecule encoding the fusion construct of claim 1.

9. An expression vector comprising the nucleic acid molecule of claim 8 under control of an appropriate promoter.

10. The expression vector of claim 9, which is a procaryotic expression vector.

11. The expression vector of claim 9, which is a eucaryotic expression vector.

12. A host cell comprising the expression vector of claim 10.

13. The host cell of claim 12, which is an *E. coli* cell.

14. A host cell comprising the expression vector of claim 11.

15. The host cell of claim 14, which is a HEK cell.

16. Diagnostic agent comprising the fusion construct of claim 1.

17. A chimeric fusion construct comprising the extracellular portion of human FcεRIα and at least one avian constant immunoglobulin domain, wherein the at least one avian constant immunoglobulin domain is an IgY constant domain or a combination of IgY domains, and wherein one or more glycosylation site(s) of the immunoglobulin domain(s) is(are) mutated by site-directed mutatgenesis.

18. The fusion construct of claim 17, wherein the IgY constant domain(s) is(are) monoglycosylated.

19. The fusion construct of claim 17, wherein the IgY constant domain(s) is(are) non-glycosylated.

* * * * *